(12) United States Patent
Ferrari et al.

(10) Patent No.: US 6,979,469 B2
(45) Date of Patent: Dec. 27, 2005

(54) USE OF POLYAMIDE POLYMER IN A MASCARA COMPOSITION COMPRISING AT LEAST ONE INERT FILLER

(75) Inventors: Véronique Ferrari, Maisons-Alfort (FR); Richard Kolodziej, Paris (FR)

(73) Assignee: L'Oréal, S.A., Paris (FR)

( * ) Notice: Subject to any disclaimer, the term of this patent is extended or adjusted under 35 U.S.C. 154(b) by 322 days.

(21) Appl. No.: 10/203,018

(22) PCT Filed: Dec. 12, 2001

(86) PCT No.: PCT/IB01/02833

§ 371 (c)(1),
(2), (4) Date: Mar. 24, 2003

(87) PCT Pub. No.: WO02/47625

PCT Pub. Date: Jun. 20, 2002

(65) Prior Publication Data

US 2004/0131647 A9 Jul. 8, 2004
US 2004/0202683 A2 Jul. 8, 2004

(30) Foreign Application Priority Data

Dec. 12, 2000 (WO) .............................. PCT/IB00/02000

(51) Int. Cl.$^7$ ............................................... A61K 7/48
(52) U.S. Cl. ......................... 424/707; 424/65; 424/64; 424/401
(58) Field of Search .............................. 424/70.7, 401, 424/63, 64

(56) References Cited

U.S. PATENT DOCUMENTS

| | | |
|---|---|---|
| 2,379,413 A | 7/1945 | Bradley |
| 2,450,940 A | 10/1948 | Cowan et al. |
| 2,662,068 A | 12/1953 | Floyd |
| 2,663,649 A | 12/1953 | Winkler |
| 2,890,097 A | 6/1959 | Coe |
| 2,962,461 A | 11/1960 | Toussaint et al. |
| 3,086,914 A | 4/1963 | Soloway |
| 3,141,787 A | 7/1964 | Goetze et al. |
| 3,148,125 A | 9/1964 | Strianse et al. |
| 3,156,572 A | 11/1964 | Carlick et al. |

(Continued)

FOREIGN PATENT DOCUMENTS

| | | |
|---|---|---|
| CA | 1319306 | 6/1988 |
| CA | 2003346 | 5/1990 |
| DE | 38 39 136 A1 | 5/1990 |
| DE | 38 43 892 | 6/1990 |
| DE | 42 08 297 | 9/1993 |
| DE | 42 34 886 | 4/1994 |
| DE | 195 43 988 | 5/1997 |
| DE | 197 07 309 A1 | 8/1998 |
| DE | 197 50 246 A1 | 5/1999 |
| DE | 199 51 010 | 4/2001 |

(Continued)

OTHER PUBLICATIONS

English language DERWENT abstract of EP 0 169 997 B.
English language DERWENT abstract of EP 0 820 764 A1.
English language DERWENT abstract of EP 0 923 928 A1.
English language DERWENT abstract of EP 0 925 780 A1.
English language DERWENT abstract of EP 0 943 340 A1.
English language DERWENT abstract of EP 1 068 856 A1.
English language DERWENT abstract of FR 2 796 270.
English language DERWENT abstract of FR 2 796 271.
English language DERWENT abstract of FR 2 796 272.
English language DERWENT abstract of FR 2 796 273.
English language DERWENT abstract of FR 2 796 276.
English language DERWENT abstract of FR 2 804 017.
English language DERWENT abstract of FR 2 804 018.
English language DERWENT abstract of FR 2 810 562.
English language DERWENT abstract of FR 2 811 225.
English language DERWENT abstract of FR 2 811 552 A1.
English language DERWENT abstract of FR 2 816 506.
English language DERWENT abstract of FR 2 817 739.
English language DERWENT abstract of FR 2 817 740.
English language DERWENT abstract of FR 2 817 743.
English language DERWENT abstract of FR 2 819 399.
English language DERWENT abstract of FR 2 819 400.
English language DERWENT abstract of JP 02/200612.

(Continued)

*Primary Examiner*—Jyothsna Venkat
(74) *Attorney, Agent, or Firm*—Finnegan, Henderson, Farabow, Garrett & Dunner, L.L.P.

(57) ABSTRACT

A physiologically acceptable, in particular mascara, cosmetic composition comprising at least one polymer, such as a structuring polymer, chosen from polymers of following formula (I):

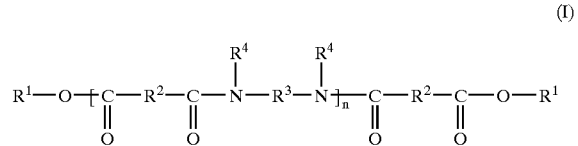

in which n denotes a number of amide units, such that the number of ester groups represents from 10% to 50% of the total number of ester and amide groups; $R^1$ is, in each case, independently an alkyl or alkenyl group having at least 4 carbon atoms; $R^2$ independently represents, in each case, a $C_4$ to $C_{42}$ hydrocarbonaceous group, provided that 50% of the $R^2$ groups represent a $C_{30}$ to $C_{42}$ hydrocarbonaceous group, $R^3$ independently represents, in each case, an organic group provided with at least 2 carbon atoms, with hydrogen atoms and optionally with one or more oxygen or nitrogen atoms; and $R^4$ independently represents, in each case, a hydrogen atom, a $C_1$ to $C_{10}$ alkyl group or a direct bond to $R^3$ or another $R^4$, so that the nitrogen atom to which both $R^3$ and $R^4$ are bonded forms part of a heterocyclic structure defined by $R^4$—N—$R^3$, with at least 50% of the $R^4$ groups representing a hydrogen atom and at least one inert filler.

7 Claims, No Drawings

U.S. PATENT DOCUMENTS

| | | |
|---|---|---|
| 3,255,082 A | 6/1966 | Barton |
| 3,341,465 A | 9/1967 | Kaufman et al. |
| 3,412,115 A | 11/1968 | Floyd et al. |
| 3,615,289 A | 10/1971 | Felton |
| 3,645,705 A | 2/1972 | Miller et al. |
| 3,778,394 A | 12/1973 | Lovald et al. |
| 3,819,342 A | 6/1974 | Gunderman et al. |
| 3,857,960 A | 12/1974 | Mackles |
| 3,926,655 A | 12/1975 | Miles |
| 3,937,811 A | 2/1976 | Papantoniou et al. |
| 3,969,087 A | 7/1976 | Saito et al. |
| 4,049,792 A | 9/1977 | Elsnau |
| 4,051,159 A | 9/1977 | Tsoucalas et al. |
| 4,062,819 A | 12/1977 | Mains et al. |
| RE29,871 E | 12/1978 | Papantoniou et al. |
| 4,128,436 A | 12/1978 | O'Hara et al. |
| 4,137,306 A | 1/1979 | Rubino et al. |
| 4,150,002 A | 4/1979 | Drawert et al. |
| 4,275,054 A | 6/1981 | Sebag et al. |
| 4,275,055 A | 6/1981 | Nachtigal et al. |
| 4,278,658 A | 7/1981 | Hooper et al. |
| 4,279,658 A | 7/1981 | Harvey et al. |
| 4,337,298 A | 6/1982 | Karim et al. |
| 4,341,671 A | 7/1982 | Bolze et al. |
| 4,376,194 A | 3/1983 | Tanaka et al. |
| 4,387,090 A | 6/1983 | Bolich, Jr. |
| 4,438,240 A | 3/1984 | Tanaka et al. |
| 4,466,936 A | 8/1984 | Schapel |
| 4,536,405 A | 8/1985 | Nara et al. |
| 4,552,693 A | 11/1985 | Hussain et al. |
| 4,571,267 A | 2/1986 | Drawert et al. |
| 4,655,836 A | 4/1987 | Drawert et al. |
| 4,663,428 A | 5/1987 | Okitu et al. |
| 4,699,779 A | 10/1987 | Palinczar |
| 4,712,571 A | 12/1987 | Remz et al. |
| 4,769,285 A | 9/1988 | Rasmussen |
| 4,806,338 A | 2/1989 | Smith |
| 4,806,345 A | 2/1989 | Bhattacharyya |
| 4,820,765 A | 4/1989 | Whyzmuzis |
| 4,871,536 A | 10/1989 | Arraudeau et al. |
| 4,937,069 A | 6/1990 | Shin |
| 4,952,245 A | 8/1990 | Iwano et al. |
| 5,069,897 A | 12/1991 | Orr |
| 5,102,656 A | 4/1992 | Kasat |
| 5,186,318 A | 2/1993 | Oestreich et al. |
| 5,223,559 A | 6/1993 | Arraudeau et al. |
| 5,272,241 A | 12/1993 | Lucarelli et al. |
| 5,302,398 A | 4/1994 | Egidio et al. |
| 5,342,894 A | 8/1994 | Robeson et al. |
| 5,362,482 A | 11/1994 | Yoneyama et al. |
| 5,372,852 A | 12/1994 | Titterington et al. |
| 5,389,363 A | 2/1995 | Snyder et al. |
| 5,472,686 A | 12/1995 | Tsubaki et al. |
| 5,500,209 A | 3/1996 | Ross et al. |
| 5,505,937 A | 4/1996 | Castrogiovanni et al. |
| 5,510,452 A | 4/1996 | Santhanam |
| 5,536,871 A | 7/1996 | Santhanam |
| 5,538,718 A | 7/1996 | Aul et al. |
| 5,538,793 A | 7/1996 | Inokuchi et al. |
| 5,540,853 A | 7/1996 | Trinh et al. |
| 5,603,925 A | 2/1997 | Ross et al. |
| 5,610,199 A | 3/1997 | Cohen et al. |
| 5,612,043 A | 3/1997 | Deprez et al. |
| 5,616,331 A | 4/1997 | Allard et al. |
| 5,618,523 A | 4/1997 | Zysman et al. |
| 5,620,693 A | 4/1997 | Piot et al. |
| 5,645,632 A | 7/1997 | Pavlin |
| 5,667,770 A | 9/1997 | Szweda et al. |
| 5,679,357 A | 10/1997 | Dubief et al. |
| 5,683,817 A | 11/1997 | Kenmochi |
| 5,719,255 A | 2/1998 | Heucher et al. |
| 5,747,625 A | 5/1998 | Furukawa et al. |
| 5,750,125 A | 5/1998 | Lahanas et al. |
| 5,750,127 A | 5/1998 | Rokitowski |
| 5,750,489 A | 5/1998 | Garcia et al. |
| 5,780,517 A | 7/1998 | Cohen et al. |
| 5,783,657 A * | 7/1998 | Pavlin et al. ............... 528/310 |
| 5,800,816 A | 9/1998 | Brieva et al. |
| 5,807,968 A | 9/1998 | Heinrich et al. |
| 5,830,483 A | 11/1998 | Seidel et al. |
| 5,837,223 A | 11/1998 | Barone et al. |
| 5,849,275 A | 12/1998 | Calello et al. |
| 5,849,278 A | 12/1998 | Piot et al. |
| 5,849,333 A | 12/1998 | Nordhauser et al. |
| 5,851,517 A | 12/1998 | Mougin et al. |
| 5,857,903 A | 1/1999 | Ramspeck et al. |
| 5,858,338 A | 1/1999 | Piot et al. |
| 5,866,149 A | 2/1999 | Piot et al. |
| 5,871,764 A | 2/1999 | Diaz et al. |
| 5,874,069 A | 2/1999 | Mendolia et al. |
| 5,882,363 A | 3/1999 | Spaulding et al. |
| 5,891,424 A | 4/1999 | Bretzler et al. |
| 5,897,869 A | 4/1999 | Roulier et al. |
| 5,902,592 A | 5/1999 | Bara et al. |
| 5,908,631 A | 6/1999 | Arnaud et al. |
| 5,911,974 A | 6/1999 | Brieva et al. |
| 5,919,441 A | 7/1999 | Mendolia et al. |
| 5,925,337 A | 7/1999 | Arraudeau et al. |
| 5,945,095 A | 8/1999 | Mougin et al. |
| 5,945,112 A | 8/1999 | Flynn et al. |
| 5,959,009 A | 9/1999 | Konik et al. |
| 5,961,998 A | 10/1999 | Arnaud et al. |
| 5,965,112 A | 10/1999 | Brieva et al. |
| 5,972,354 A | 10/1999 | de la Poterie et al. |
| 5,972,359 A | 10/1999 | Sine et al. |
| 5,976,514 A | 11/1999 | Guskey et al. |
| 5,981,680 A | 11/1999 | Petroff et al. |
| 5,985,298 A | 11/1999 | Brieva et al. |
| 5,998,570 A | 12/1999 | Pavlin et al. |
| 6,004,567 A | 12/1999 | Marchi-Lemann et al. |
| 6,007,799 A | 12/1999 | Lee et al. |
| 6,019,962 A | 2/2000 | Rabe et al. |
| 6,036,947 A | 3/2000 | Barone et al. |
| 6,045,823 A | 4/2000 | Vollhardt et al. |
| 6,051,216 A | 4/2000 | Barr et al. |
| 6,054,517 A | 4/2000 | Spaulding et al. |
| 6,060,072 A | 5/2000 | Konik et al. |
| 6,063,398 A | 5/2000 | Gueret |
| 6,074,654 A | 6/2000 | Drechsler et al. |
| 6,103,249 A | 8/2000 | Roulier et al. |
| 6,106,820 A | 8/2000 | Morrissey et al. |
| 6,111,055 A | 8/2000 | Berger et al. |
| 6,156,325 A | 12/2000 | Farer et al. |
| 6,156,804 A | 12/2000 | Chevalier et al. |
| 6,165,454 A | 12/2000 | Patel et al. |
| 6,165,971 A | 12/2000 | Oppenlander et al. |
| 6,177,523 B1 | 1/2001 | Reich et al. |
| 6,180,117 B1 | 1/2001 | Berthiaume et al. |
| 6,180,123 B1 | 1/2001 | Mondet |
| 6,190,673 B1 | 2/2001 | Guskey et al. |
| 6,197,100 B1 | 3/2001 | Melbouci |
| 6,203,780 B1 | 3/2001 | Arnaud et al. |
| 6,203,807 B1 | 3/2001 | Lemann |
| 6,214,329 B1 * | 4/2001 | Brieva et al. ............... 424/70.7 |
| 6,221,389 B1 | 4/2001 | Cannell et al. |
| 6,242,509 B1 | 6/2001 | Berger et al. |
| 6,251,375 B1 | 6/2001 | Bara |
| 6,251,409 B1 | 6/2001 | Hegyi et al. |
| 6,254,876 B1 | 7/2001 | de la Poterie et al. |
| 6,254,877 B1 | 7/2001 | De La Poterie et al. |
| 6,264,933 B1 | 7/2001 | Bodelin et al. |

| US Patent | Date | Inventor |
|---|---|---|
| 6,268,466 B1 | 7/2001 | MacQueen et al. |
| 6,280,846 B1 | 8/2001 | Darby et al. |
| 6,287,552 B1 | 9/2001 | Tournilhac et al. |
| 6,325,994 B1 | 12/2001 | Collin et al. |
| 6,348,563 B1 | 2/2002 | Fukuda et al. |
| 6,372,235 B1 | 4/2002 | Livoreil et al. |
| 6,376,078 B1 | 4/2002 | Inokuchi |
| 6,383,502 B1 | 5/2002 | Dunshee et al. |
| 6,399,081 B1 | 6/2002 | Nakanishi et al. |
| 6,402,408 B1 * | 6/2002 | Ferrari ................. 401/64 |
| 6,423,306 B2 | 7/2002 | Caes et al. |
| 6,423,324 B1 | 7/2002 | Murphy et al. |
| 6,432,391 B1 | 8/2002 | Bara |
| 6,469,131 B2 | 10/2002 | Lawson et al. |
| 6,475,500 B2 | 11/2002 | Vatter et al. |
| 6,479,686 B2 | 11/2002 | Nakanishi et al. |
| 6,482,400 B1 | 11/2002 | Collin |
| 6,491,931 B1 | 12/2002 | Collin |
| 6,497,861 B1 | 12/2002 | Wang et al. |
| 2001/0014312 A1 | 8/2001 | Nakanishi et al. |
| 2001/0014313 A1 | 8/2001 | Roulier et al. |
| 2001/0028887 A1 | 10/2001 | Douin et al. |
| 2001/0031280 A1 | 10/2001 | Ferrari et al. |
| 2001/0033846 A1 | 10/2001 | Roulier et al. |
| 2002/0044918 A1 | 4/2002 | Bara |
| 2002/0058053 A1 | 5/2002 | Nakanishi et al. |
| 2002/0081323 A1 | 6/2002 | Nakanishi et al. |
| 2002/0102225 A1 | 8/2002 | Hess et al. |
| 2002/0107314 A1 | 8/2002 | Pinzon et al. |
| 2002/0111330 A1 | 8/2002 | Pinzon et al. |
| 2002/0114771 A1 | 8/2002 | Nakanishi |
| 2002/0114773 A1 | 8/2002 | Kanji et al. |
| 2002/0119171 A1 | 8/2002 | Gruning et al. |
| 2002/0120036 A1 | 8/2002 | Pinzon et al. |
| 2002/0122781 A1 | 9/2002 | Pinzon et al. |
| 2002/0131947 A1 | 9/2002 | Nakanishi |
| 2002/0141958 A1 | 10/2002 | Maio et al. |
| 2002/0150602 A1 | 10/2002 | Livoreil et al. |
| 2002/0159964 A1 | 10/2002 | Nakanishi et al. |
| 2002/0168335 A1 | 11/2002 | Collin |
| 2002/0172696 A1 | 11/2002 | Ferrari |
| 2002/0189030 A1 | 12/2002 | Collin |
| 2002/0192168 A1 | 12/2002 | Blin et al. |
| 2003/0012764 A1 | 1/2003 | Collin |
| 2003/0026772 A1 | 2/2003 | Jager-Lezer et al. |
| 2003/0044367 A1 | 3/2003 | Simon et al. |

FOREIGN PATENT DOCUMENTS

| | | |
|---|---|---|
| EP | 0 295 886 B1 | 12/1988 |
| EP | 0 370 470 B1 | 5/1990 |
| EP | 0 374 332 A1 | 6/1990 |
| EP | 0 412 710 B1 | 2/1991 |
| EP | 0 444 633 A2 | 9/1991 |
| EP | 0 557 196 A1 | 8/1993 |
| EP | 0 602 905 B1 | 6/1994 |
| EP | 0 609 132 B1 | 8/1994 |
| EP | 0 623 670 A2 | 11/1994 |
| EP | 0 628 582 B1 | 12/1994 |
| EP | 0 673 642 B1 | 9/1995 |
| EP | 0 708 114 A1 | 4/1996 |
| EP | 0 749 746 A1 | 12/1996 |
| EP | 0 749 747 A1 | 12/1996 |
| EP | 0 749 748 | 12/1996 |
| EP | 0 775 483 A1 | 5/1997 |
| EP | 0 797 976 A2 | 10/1997 |
| EP | 0 847 752 | 6/1998 |
| EP | 0 877 063 B1 | 11/1998 |
| EP | 0 879 592 A2 | 11/1998 |
| EP | 0 887 073 A1 | 12/1998 |
| EP | 0 928 608 A2 | 7/1999 |
| EP | 0 930 058 B1 | 7/1999 |
| EP | 0 930 060 A1 | 7/1999 |
| EP | 0 958 085 B1 | 11/1999 |
| EP | 0 958 804 A2 | 11/1999 |
| EP | 0 958 805 A2 | 11/1999 |
| EP | 0 958 811 A1 | 11/1999 |
| EP | 0 959 066 A2 | 11/1999 |
| EP | 0 959 091 A1 | 11/1999 |
| EP | 0 976 390 A1 | 2/2000 |
| EP | 0 984 025 A2 | 3/2000 |
| EP | 1 002 514 A1 | 5/2000 |
| EP | 1 031 342 A1 | 8/2000 |
| EP | 1 048 282 A1 | 11/2000 |
| EP | 1 053 742 A1 | 11/2000 |
| EP | 1 062 944 A1 | 12/2000 |
| EP | 1 062 959 A1 | 12/2000 |
| EP | 1 064 919 A1 | 1/2001 |
| EP | 1 064 920 A1 | 1/2001 |
| EP | 1 066 814 A1 | 1/2001 |
| EP | 1 068 854 A1 | 1/2001 |
| EP | 1 068 855 A1 | 1/2001 |
| EP | 1 086 945 A1 | 3/2001 |
| EP | 1 090 627 B1 | 4/2001 |
| EP | 1 095 959 A2 | 5/2001 |
| EP | 1 114 636 A1 | 7/2001 |
| EP | 1 213 011 A1 | 6/2002 |
| EP | 1 213 316 A2 | 6/2002 |
| FR | 1 529 329 | 5/1968 |
| FR | 2 232 303 | 1/1975 |
| FR | 2 674 126 | 9/1992 |
| FR | 2 785 179 | 5/2000 |
| FR | 2 802 806 | 6/2001 |
| FR | 2 819 402 | 7/2002 |
| GB | 1 117 129 | 6/1968 |
| GB | 1 194 901 | 6/1970 |
| GB | 1 194 902 | 6/1970 |
| GB | 1 220 069 | 1/1971 |
| GB | 1 273 004 | 5/1972 |
| GB | 1 444 204 | 7/1976 |
| GB | 2 014 852 | 9/1979 |
| GB | 2 021 411 A | 12/1979 |
| GB | 2 147 305 A | 5/1985 |
| GB | 2 196 978 A | 5/1998 |
| JP | 53043577 A | 4/1978 |
| JP | 56123909 A | 9/1981 |
| JP | 56166276 A | 12/1981 |
| JP | 61065809 A | 4/1986 |
| JP | 2127568 A | 5/1990 |
| JP | 2216279 A | 8/1990 |
| JP | 3014683 A | 1/1991 |
| JP | 04346909 A | 12/1992 |
| JP | 7179795 A | 7/1995 |
| JP | 7267827 A | 10/1995 |
| JP | 8225316 A | 9/1996 |
| JP | 9020631 | 1/1997 |
| JP | 9295922 A | 11/1997 |
| JP | 10120903 | 5/1998 |
| JP | 10/212213 | 8/1998 |
| JP | 10259344 A | 9/1998 |
| JP | 11106216 A | 4/1999 |
| JP | 11335228 | 12/1999 |
| JP | 11335242 | 12/1999 |
| JP | 11335254 | 12/1999 |
| JP | 200038314 | 2/2000 |
| JP | 200038316 | 2/2000 |
| JP | 200038317 | 2/2000 |
| JP | 200038321 | 2/2000 |
| JP | 200086427 | 3/2000 |
| JP | 200086429 | 3/2000 |
| JP | 200086438 | 3/2000 |
| WO | WO 86/04916 | 8/1986 |
| WO | WO 87/03783 | 7/1987 |

| WO | WO 91/12793 | 9/1991 |
| WO | WO 93/21763 | 11/1993 |
| WO | WO 93/23008 | 11/1993 |
| WO | WO 94/18261 | 8/1994 |
| WO | WO 94/21233 | 9/1994 |
| WO | WO 95/15741 | 6/1995 |
| WO | WO 95/24887 | 9/1995 |
| WO | WO 95/33000 | 12/1995 |
| WO | WO 96/15761 | 5/1996 |
| WO | WO 96/40044 | 12/1996 |
| WO | WO 97/17057 | 5/1997 |
| WO | WO 97/36573 | 10/1997 |
| WO | WO 98/17243 | 4/1998 |
| WO | WO 98/17705 | 4/1998 |
| WO | WO 98/22078 | 5/1998 |
| WO | WO 98/27162 | 6/1998 |
| WO | WO 98/42298 | 10/1998 |
| WO | WO 98/47470 | 10/1998 |
| WO | WO 98/52534 | 11/1998 |
| WO | WO 98/58623 | 12/1998 |
| WO | WO 99/24002 | 5/1999 |
| WO | WO 00/40216 | 7/2000 |
| WO | WO 00/61080 | 10/2000 |
| WO | WO 00/61081 | 10/2000 |
| WO | WO 00/74519 A2 | 12/2000 |
| WO | WO 01/51020 | 7/2001 |
| WO | WO 01/97758 A2 | 12/2001 |
| WO | WO 02/03932 A2 | 1/2002 |
| WO | WO 02/03935 A2 | 1/2002 |
| WO | WO 02/03950 A2 | 1/2002 |
| WO | WO 02/03951 A2 | 1/2002 |
| WO | WO 02/47605 A2 | 6/2002 |
| WO | WO 02/47608 A2 | 6/2002 |
| WO | WO 02/47619 A2 | 6/2002 |
| WO | WO 02/47620 | 6/2002 |
| WO | WO 02/47627 A1 | 6/2002 |
| WO | WO 02/47658 | 6/2002 |
| WO | WO 02/49583 A1 | 6/2002 |
| WO | WO 02/49601 A1 | 6/2002 |
| WO | WO 02/055030 A2 | 7/2002 |
| WO | WO 02/055031 A1 | 7/2002 |
| WO | WO 02/056845 A1 | 7/2002 |
| WO | WO 02/092047 A1 | 11/2002 |
| WO | WO 02/092663 A1 | 11/2002 |
| WO | WO 02/102322 A2 | 12/2002 |

OTHER PUBLICATIONS

English language DERWENT abstract of JP 02/255560.

English language DERWENT abstract of JP 10/007527.

English language DERWENT abstract of JP 10/212213.

English language DERWENT abstract of JP 62/061911.

International Search Report in PCT/US 01/47454, dated Aug. 29, 2002.

International Search Report in PCT/US 01/47499, dated Aug. 8, 2002.

Kenji Hanabusa et al., Easy Preparation and Prominent Gelation of New Gelator Based on L–Lysine, 2000 Chem. Letters, 1070–1071.

Kenji Hanabusa et al., Prominent Gelation and Chiral Aggregation of Alkylamides Derived from trans–1,2–Diaminocyclohexane, Angew. Chem. Int. Ed. Engl. 1996, 35, No. 17, 1949–1951.

Kenji Hanabusa et al., Terephthaloyl Derivatives as New Gelators; Excellent Gelation Ability and Remarkable Increase of Gel Strength by Adding Polymers, 1999 Chemistry Letters 767–768.

Milan Jokic et al., A Novel Type of Small Organic Gelators: Bis(Amino Acid) Oxalyl Amides, 1995 J. Chem. Soc., Chem. Commun., 1723–1724.

P. Terech, "Low–Molecular Weight Organogelators," in Specialist Surfactants, ch. 8, pp. 208–268 (I.D. Robb, ed., 1997).

Partial International Search Report for PCT/US 01/47497, dated Nov. 15, 2002.

Toshimi Shimizu et al., Stereochemical Effect of Even–Odd Connecting Links on Supramolecular Assemblies Made of 1–Glucosamide Bolaamphiphiles, J. Am Chem. Soc. 1997, 119, 2812–2818.

Xuzhong Luo et al., Self–assembled organogels formed by monoalkyl derivatives of oxamide, 2000 Chem. Commun. 2091–92.

English language DERWENT abstract of FR 2 232 303.
English language DERWENT abstract of JP 61065809.
English language DERWENT abstract of FR 2 674 126.
English language DERWENT abstract of JP 04346909.
English language DERWENT abstract of EP 0 557 196 A1.
English language DERWENT abstract of EP 0 609 132.
English language DERWENT abstract of JP 7267827.
English language DERWENT abstract of JP 8225316.
English language DERWENT abstract of EP 0 749 746 A1.
English language DERWENT abstract of EP 0 749 747 A1.
English language DERWENT abstract of EP 0 775 483 A1.
English language DERWENT abstract of EP 0 847 752 A1.
English language DERWENT abstract of EP 0 879 592 A2.
English language DERWENT abstract of EP 0 887 073 A1.
English language DERWENT abstract of JP 11106216.
English language DERWENT abstract of EP 0 925 780 A1.
English language DERWENT abstract of EP 0 959 066 A2.
English language DERWENT abstract of EP 0 930 058 B1.
English language DERWENT abstract of EP 0 930 060 A1.
English language DERWENT abstract of EP 0 958 811 A1.
English language DERWENT abstract of EP 0 959 091 A1.
English language DERWENT abstract of EP 0 976 390 A1.
English language DERWENT abstract of EP 0 984 025 A2.
English language DERWENT abstract of FR 2 785 179.
English language DERWENT abstract of EP 1 002 514.
English language DERWENT abstract of EP 1 031 342 A1.
English language DERWENT abstract of EP 1 048 282 A1.
English language DERWENT abstract of EP 1 053 742.
English language DERWENT abstract of EP 1 064 919.
English language DERWENT abstract of EP 1 064 920.
English language DERWENT abstract of EP 1 066 814.
English language DERWENT abstract of EP 1 068 854 A1.
English language DERWENT abstract of EP 1 068 855 A1.
English language DERWENT abstract of EP 1 068 856 A1.
English language DERWENT abstract of EP 1 086 945 A1.
English language DERWENT abstract of EP 1 090 627 B1.
English language DERWENT abstract of FR 2 802 806.
English language DERWENT abstract of EP 1 114 636 A1.
English language DERWENT abstract of WO 02/055031 A1.
English language DERWENT abstract of FR 2 819 402.
English language DERWENT abstract of WO 02/056845 A1.
English language DERWENT abstract of JP 9295922 A.
English language DERWENT abstract of JP 7179795A.
English language DERWENT abstract of JP 3014683.
English language DERWENT abstract of JP 2216279.
English language DERWENT abstract of JP 2127568.
English language DERWENT abstract of JP 10259344.

English language DERWENT abstract of DE 3839136.
English language DERWENT abstract of DE 197 07 309.
English language DERWENT abstract of DE 197 50 246.
English language DERWENT abstract of EP 0 374 332 A1.
English language DERWENT abstract of JP 56166276A.
English language DERWENT abstract of JP 53043577.
English language DERWENT abstract of JP 56123909.
English language DERWENT abstract of EP 0749 748 A.
English language DERWENT abstract of DE 42 34 886 A.
English language DERWENT abstract of DE 42 08 297 A.
English language DERWENT abstract of DE 38 43 892 A.
English language DERWENT abstract of DE 195 43 988.
English language DERWENT abstract of DE 199 51 010.
English language DERWENT abstract of EP 0 958 085 B1.
English language DERWENT abstract of JP 9020631.
English language DERWENT abstract of JP 10/120903.
English language DERWENT abstract of JP 1135228.
English language DERWENT abstract of JP 11335242.
English language DERWENT abstract of JP 11335254.
English language DERWENT abstract of JP 2000038314 A.
English language DERWENT abstract of JP 2000038316 A.
English language DERWENT abstract of JP 2000038317 A.
English language DERWENT abstract of JP 2000038321 A.
English language DERWENT abstract of JP 2000086427 A.
English language DERWENT abstract of JP 2000086429 A.
English language DERWENT abstract of JP 2000086438 A.
Certified English translation of FR 1 529 329.
Handbook of Cosmetic Science. Elsevier Advanced Tech., 1$^{st}$ Edition (1994), p. 19.
Kirk–Othmer, "Encyclopedia of Chemical Technology", Third Edition, vol. 22, John Wiley & Sons, 1983, pp. 332–432.
Charles M. Hansen, "*The Three Dimensional Solubility Parameter—Key to Paint Component Affinities: I Solvents, Plasticizers, Polymers, and Resins*," Journal of Paint Technology, vol. 39, No. 505, Feb. 1967, pp. 104–117.
Yasuda et al., *Novel Low–molecular–weight Organic Gels: N,N', N'–Tristearyltrimesamide/Organic Solvent System*, Chemistry Letters, pp. 575–576, 1996, the month of publication is not available.
Bush Boake Allen, Inc., *Uniclear Formulations*, dated Oct. 13, 1998.
International Search Report in PCT/US 01/47459, dated Feb. 6, 2003.
International Search Report in PCT/US 01/47496, dated Feb. 26, 2003.
International Search Report in PCT/US01/47497, dated Dec. 2, 2002.
French Search Report in FR 9909176, dated Mar. 23, 2000.
French Search Report in FR 9909177.
French Search Report in FR 9916588, dated Oct. 16, 2000.
French Search Report in FR 0001004, dated Nov. 10, 2000.
French Search Report in FR 0000920, dated Nov. 10, 2000.
International Search Report in PCT/FR01/00229, dated Jan. 24, 2000.
French Search Report for FR 0008084, dated Mar. 28, 2001.
International Search Report in PCT/FR01/01958, dated Oct. 26, 2001.
French Search Report in FR 0008913, dated Mar. 28, 2001.
French Search Report in FR 0016161, dated Sep. 6, 2001.
International Search Report in PCT/FR01/03940, dated Mar. 13 ,2002.
French Search Report in FR 0016163, dated Aug. 1, 2001.
International Search Report in PCT/FR01/03945, dated May 31, 2002.
French Search Report PCT/FR01/03939, dated Apr. 15, 2002.
French Search Report in FR 0016164, dated Sep. 6, 2001.
International Search Report in PCT/FR01/03937, dated Apr. 23, 2002.
French Search Report in FR 0016180, dated Oct. 16, 2001.
International Search Report in PCT/FR01/03938, dated Jan. 10, 2002.
International Search Report in PCT/IB01/02780, dated Apr. 10, 2002.
International Search Report in PCT/US00/33596, dated Aug. 8, 2001.
International Search Report in PCT/IB00/02000, dated Aug. 8, 2001.
International Search Report in PCT/IB01/02833, dated May 24, 2002.
International Search Report in PCT/IB00/02006, dated Aug. 8, 2001.
International Search Report in PCT/IB01/02840, dated Jun. 11, 2002.
International Search Report in PCT/IB01/02820, dated May 27, 2002.
International Search Report in PCT/IB00/02002, dated Sep. 4, 2001.
International Search Report in PCT/IB01/02786, dated Oct. 2, 2002.
French Search Report in FR 0100479, dated Sep. 17, 2001.
International Search Report in PCT/FR02/00129, dated Jun. 14, 2002.
French Search Report in FR 0100623, dated Oct. 9, 2001.
International Search Report in PCT/FR02/00144, dated Jun. 14, 2002.
French Search Report in FR 0100620, dated Nov. 6, 2001.
International Search Report in PCT/FR02/00194, dated May 12, 2002.
French Search Report in FR 0114529, dated Aug. 26, 2002.
French Search Report in FR 0114530, dated Aug. 26, 2002.
International Search Report in PCT/FR01/03726, dated Aug. 9, 2002.
Estee Lauder MagnaScopic® Maximum Volume mascara product packaging, believed to have first been sold in 2003.
Origins Full Story™ Lush lash mascara product packaging, believed to have first been sold in 2003.

* cited by examiner

USE OF POLYAMIDE POLYMER IN A MASCARA COMPOSITION COMPRISING AT LEAST ONE INERT FILLER

The present invention relates to a care and/or treatment and/or make-up composition for the skin, including the scalp, and/or for the lips of human beings, and/or for other keratin materials, such as keratinous fibers, containing a liquid fatty phase, structured with a specific polymer containing a hetero atom. This composition is stable over time and is especially in the form of a make-up stick and more especially a foundation stick or a stick of lipstick, whose application produces a migration-resistant deposit which shows good staying power or long-wearing properties.

The foundations currently marketed are usually either in the form of a liquid packaged in a bottle, or in the form of a product compacted in a case (see, for example, U.S. Pat. No. 5,186,318). These foundations may require the use of an applicator such as a sponge, which may rapidly become contaminated and must be cleaned very regularly, especially after each application. Thus, users of foundations are increasingly on the lookout for solid foundations in stick form, in order to dispense with the sponge-type applicator. Such a foundation may be easy to use, hygienic and can be applied until all of the product has been used up, unlike a conventional foundation applied with a sponge. Furthermore, the surface of the foundation may remain smooth, whereas the surface of a product compacted in a case may become deformed under the pressure of the successive uptakes onto the applicator. Finally, a foundation in stick form may allow a uniform make-up effect to be obtained.

Conventional lipsticks and concealer products are also usually in the form of a stick, as are deodorants and lipcare or antisun lip products.

These cosmetic or dermatological products contain a structured liquid fatty phase, i.e., a phase which is gelled and/or rigidified with structural agents such as waxes.

For the purposes of the invention, the expression "liquid fatty phase" means a fatty phase which is liquid at room temperature (25° C.) and atmospheric pressure (760 mmHg, i.e 101 KPa), and comprises at least one (as used throughout herein, the expression "at least one" means one or more and thus includes individual components as well as mixtures/combinations) fatty substance that is liquid at room temperature, also referred to as an oil, that is generally mutually compatible, i.e. forming a homogeneous phase macroscopically. The expression "liquid fatty substance" means a non-aqueous liquid medium which is immiscible in all proportions with water, for example, a hydrocarbon-based compound comprising at least one carbon chain containing at least 5 carbon atoms and possibly comprising at least one polar group chosen from carboxylic acid, hydroxyl, polyol, amine, amide, phosphoric acid, phosphate, ester, ether, urea, carbamate, thiol, thioether and thioester, a silicone compound optionally comprising carbon chains at the end or pendant, these chains optionally being substituted with a group chosen from fluoro, perfluoro, (poly)amino acid, ether, hydroxyl, amine, acid and ester groups; or a fluoro or perfluoro compound such as fluorohydrocarbons or perfluorohydrocarbons containing at least 5 carbon atoms, possibly comprising a hetero atom chosen from N, O, S and P and optionally at least one polar function chosen from ether, ester, amine, acid, carbamate, urea, thiol and hydroxyl groups. In practice, the total liquid fatty phase may be present, for example, in an amount ranging from 1% to 99% by weight relative to the total weight of the composition; further examples include ranges of 5% to 99%, 5% to 95.5%, 10% to 80%, and 20% to 75%.

For the purposes of the present invention, the term "wax" means a lipophilic fatty compound that is solid at room temperature (25° C.) and atmospheric pressure (760 mmHg, i.e. 101 KPa), which undergoes a reversible solid/liquid change of state, having a melting point of greater than 40° C., for example greater than 55° C., such as up to 200° C., and having an anisotropic crystal organization in the solid state. The size of the crystals may be such that the crystals diffract and/or scatter light, giving the composition a cloudy, more or less opaque appearance. By bringing the wax to its melting point, it is possible to make it miscible with oils and to form a microscopically homogeneous mixture, but on returning the temperature of the mixture to room temperature, recrystallization of the wax in the oils of the mixture is obtained, this recrystallization being responsible for the rigidification of the liquid fatty phase.

For the purposes of the invention, the waxes are those generally used in cosmetics and dermatology; they are, for instance, chosen from waxes of natural origin, such as beeswax, carnauba wax, candelilla wax, ouricury wax, Japan wax, cork fibre wax, sugar cane wax, paraffin wax, lignite wax, microcrystalline waxes, lanolin wax, montan wax, ozokerites and hydrogenated oils such as hydrogenated jojoba oil, as well as waxes of synthetic origin, for instance polyethylene waxes derived from the polymerization or copolymerization of ethylene, waxes obtained by Fischer-Tropsch synthesis, fatty acid esters and glycerides that are solid at 40° C., for example at above 55° C., silicone waxes such as alkyl- and alkoxy-poly(di)methylsiloxanes and/or poly(di)methylsiloxane esters that are solid at 40° C., for example at above 55° C.

According to the invention, the melting point values may correspond to the melting peak measured by the "Differential Scanning Calorimetry" method with a temperature rise of 5 or 10° C./min.

Unfortunately, the waxes currently used may give the composition a greasy and oily feel and/or a greasy and lank sensation. Furthermore, manufacturing a stick with waxes often poses problems of reproducibility on account of the melting point variability of the various waxes that are commercially available.

Now, the structuring of the liquid fatty phase with waxes makes it possible, in addition to obtaining a product in the form of a stick, to limit the exudation of the fatty phase from the solid compositions, especially in hot and humid regions, and to limit, after deposition on the skin or the lips, the migration of this phase in the wrinkles and fine lines, which is particularly sought after for a lipstick, a concealer product or an eyeshadow. Specifically, large migration of the liquid fatty phase, in particular when it is charged with coloring agents, may lead to an unpleasant appearance around the lips and the eyes, which particularly makes the wrinkles and fine lines more prominent. This migration is often mentioned by consumers as being a major defect of conventional lipsticks, concealer products and eye make-ups in stick form. The term "migration" means a running of the composition beyond the initial application line.

The structuring of the liquid fatty phase and the limitation of its exudation and of the migration of the deposit on the skin or the lips may increase as the wax content increases. Thus, the content of these structuring agents may be a constraining factor on the comfort, reproducibility, non greasy sensation and lightness of make-up products in stick form.

Furthermore, make-up compositions should have good staying power or long wearing properties over time and in particular of the color. Poor staying power is characterized by a color change (turning, fading) or a non-uniform change in the make-up effect over time, generally following an interaction with sebum and/or sweat secreted by the skin, and, for the lips, an interaction with saliva. Specifically, a composition which does not have good staying power or long-wearing properties over time may oblige the user to reapply the make-up regularly. However, consumers nowadays wish to enhance the beauty of their face or body while spending as little time as possible in doing so.

To overcome at least one of these drawbacks, the present inventors have envisaged replacing all or some of the waxes with polymers for structuring the liquid fatty phase, for example, of the polyamide, polyurea or polyurethane type. Unfortunately, the sticks obtained may have a greater or lesser tendency to exude, in particular in a hot and humid environment, and/or to become brittle when applied to the lips or the skin. This embrittlement may be reflected by breakage of the stick, during its shear on application.

Furthermore, the majority of make-up or care compositions, when applied to the skin, the eyelashes or the lips, may have the drawback of transferring, i.e., of being at least partly deposited and leaving marks on certain supports with which they may come into contact, such as a glass, a cup, a cigarette, an item of clothing or the skin. This may result in mediocre persistence of the film applied, making it necessary to reapply the composition regularly, such as a foundation or a lipstick. However, as noted above, users nowadays wish to achieve beauty enhancement of their face, including the lips, and their body while spending as little time as possible in doing so. Moreover, the appearance of these unacceptable marks, e.g., on shirt collars, can put certain consumers off using this type of make-up.

Cosmeticians have been interested in "transfer-resistant" lipstick compositions for several years, and more recently in "transfer-resistant" foundation compositions. Thus, in its patent application JP-A-61-65809, the company Shiseido envisaged "transfer-resistant" lipstick compositions containing a siloxysilicate resin (with a three-dimensional network), a volatile silicone oil containing a cyclic silicone chain and pulverulent fillers. Similarly, in document JP-A-62-61911, the company Noevier disclosed "transfer-resistant" lipstick, eyeliner and foundation compositions comprising one or more volatile silicones combined with one or more hydrocarbon-based waxes.

Although these compositions have improved "transfer-resistance" properties, they have the drawback of leaving on the lips, after the silicone oils have evaporated off, a film which becomes uncomfortable over time (sensation of drying out the lips and of tautness), a characteristic which puts a certain number of consumers off using this type of lipstick.

The need thus remains for a composition which does not have at least one of the above drawbacks, for example, which has at least one of good mechanical and thermal stability over time, even in hot and humid countries, and which produces a deposit on the skin or the lips that has at least one of the following characteristics: shows good staying power over time, does not migrate, and does not transfer. Furthermore, this composition should be easy to manufacture and, in an embodiment of the invention, gives the deposit at least one of a comfortable and non-greasy sensation, both during application and over time.

Accordingly, in one aspect, the present invention is drawn to a care and/or make-up and/or treatment composition for the skin and/or the lips of the face and/or for superficial body growths, such as nails or keratinous fibres, such as hair, which may make it possible to overcome at least one of the drawbacks mentioned above. It is to be noted that a deodorant product is a body hygiene product and does not relate to care, make-up or treatment of keratin materials, including keratinous fibers, skin, or lips.

The inventors have found, surprisingly, that the use of specific polymers combined with at least one filler may make it possible to obtain a composition in rigid form such as a stick, whose application to the skin or the lips produces a deposit which has noteworthy cosmetic properties. For example, the deposit may be at least one of supple, comfortable, light and "migration-resistant". In addition, in the presence of volatile solvent, the composition may show good transfer-resistance properties.

Moreover, the composition may be stable over time, may withstand shear during application and may not exude at room temperature or at elevated temperature (40 to 47° C. approximately); it can be heat stable. In addition, it can have a pleasant, fondant texture and can slide easily on the skin or the lips without being greasy.

The expression "heat stable" means a composition which does not exude at room temperature for at least 2 months, such as, for example, for at least 9 months, or at 37° C. or at 47° C. for one month.

The invention applies not only to make-up products for the lips, such as lipsticks, lip glosses and lip pencils, but also to care and/or treatment products for the skin, including the scalp, and for the lips, such as antisun products, for example in stick form for facial skin or the lips, care products for the human face or body, make-up products for the skin, both of the human face and body, such as foundations optionally cast in stick or dish form, concealer products, blushers, makeup removing, eyeshadows, face powders, transfer tattoos, body hygiene products such as deodorants, e.g., in stick form, shampoos, conditioners and make-up products for the eyes such as eyeliners, eye pencils and mascaras, e.g., In cake form, as well as make-up and care products for superficial body growths, for instance keratinous fibers such as the hair, the eyelashes and the eyebrows, or nails.

More specifically, the present invention is drawn to a composition containing at least one liquid fatty which comprises at least one structuring polymer comprising a polymer skeleton which comprises at least one hydrocarbon-based repeating unit comprising at least one hetero atom.

The at least one liquid fatty phase further contains at least one inert filler. The at least one liquid fatty phase, the at least one structuring polymer and the at least one inert filler form a physiologically acceptable medium.

In one embodiment, the at least one structuring polymer has a weight-average molecular mass of less than 100 000. However, this weight-average molecular mass can represent up to 500 000 and even up to 1 000 000.

In one aspect, the present invention is drawn to a structured composition containing at least one liquid fatty phase structured with at least one structuring polymer comprising a polymer skeleton comprising at least one hydrocarbon-based repeating unit comprising at least one hetero atom. In one embodiment, the at least one structuring polymer further comprises at least one terminal fatty chain, optionally functionalized, comprising at least one chain chosen from alkyl and alkenyl chains, such as alkyl and alkenyl chains comprising at least 4 carbons atoms, and further such as alkyl and alkeny chains comprising from 8 to 120 carbon atoms, bonded to the polymer skeleton via at least one linking group. The at least one structuring polymer may also further comprise at least one pendant fatty chain, optionally functionalized, comprising at least one chain chosen from alkyl and alkenyl chains, such as alkyl and alkenyl chains comprising at least 4 carbons atoms, and further such as alkyl and alkeny chains comprising from 8 to 120 carbon atoms, bonded to any carbon or hetero atom of the polymer skeleton via at least one linking group. The at least one structuring polymer may comprise both at least one pendant fatty chain and at least one terminal fatty chain as defined above. The at least one liquid fatty phase further contains at least one inert filler. The at least one liquid fatty phase, the at least one structuring polymer and the at least one inert filler form a physiologically acceptable medium.

The composition of the invention can be in the form of a paste, a solid or a more or less viscous cream. It can be a single or multiple emulsion, such as an oil-in-water or water-in-oil emulsion or an oil-in-water-in-oil emulsion, or a rigid or soft gel containing an oily continuous phase. For example, the liquid fatty phase can be the continuous phase of the composition. In one embodiment, the composition is anhydrous. In one embodiment, the composition is in a form cast as a stick or in a dish, for example, solid and further example in the form of an oily rigid gel, such as an anhydrous gel, e.g., an anhydrous stick. In a further embodiment, the composition is in the form of an opaque or translucent rigid gel (depending on the presence or absence of pigments), and in a specific example, the liquid fatty phase forms the continuous phase. In One embodiment, the composition is chosen from molded and poured sticks.

The structuring of the liquid fatty phase can be modified according to the nature of the polymer containing a hetero atom and of the inert filler used, and may be such that a rigid structure in the form of a stick with good mechanical strength is obtained. When these sticks are colored, they may make it possible, after application, to obtain a uniformly colored glossy deposit which does not migrate and which has good staying power or long-wearing properties, in particular of the color, over time.

The composition of the invention may, for example, be a composition for the skin or the lips, such as a foundation composition, concealer product, eyeshadow or lipstick composition, e.g., in stick form.

Structuring polymer

In one embodiment, the at least one structuring polymer in the composition of the invention is a solid that is not deformable at room temperature (25° C.) and atmospheric pressure (760 mmHg, i.e. 101 KPa). In a further embodiment, the at least one structuring polymer is capable of structuring the composition without opacifying it. The inventors think that is due to the fact that the polymer does not crystallise. Moreover, the structuration of the liquid fatty phase is due to hydrogen interactions between two molecules of polymer and/or between the polymer and the liquid fatty phase. As defined above, the at least one structuring polymer of the present invention comprises a polymer skeleton comprising at least one hydrocarbon-based repeating unit comprising at least one hetero atom. In one embodiment, the at least one structuring polymer further comprises at least one terminal fatty chain chosen from alkyl and alkenyl chains, such as of at least 4 atoms, and further such as comprising 8 to 120 carbon atoms, bonded to the polymer skeleton via at least one linking group. The terminal fatty chain may, for example, be functionalized. The at least one structuring polymer may also further comprise at least one pendant fatty chain chosen from alkyl and alkenyl chains, such as of at least 4 atoms, and further such as comprising 8 to 120 carbon atoms, bonded to any carbon or hetero atom of the polymer skeleton via at least one linking group. The pendant fatty chain may, for example, be functionalized. The at least one structuring polymer may comprise both at least one pendant fatty chain and at least one terminal fatty chain as defined above, and one or both types of chains can be functionalized.

In one embodiment, the structuring polymer comprises at least two hydrocarbon-based repeating units. As a further example, the structuring polymer comprises at least three hydrocarbon-based repeating units and as an even further example, the at least three repeating units are identical.

As used herein, "functionalized" means comprising at least one functional group. Non-limiting examples of functional groups include hydroxyl groups, ether groups, oxyalkylene groups, polyoxyalkylene groups, carboxylic acid groups, amine groups, amide groups, halogen containing groups, including fluoro and perfluoro groups, halogen atoms, ester groups, siloxane groups and polysiloxane groups.

For purposes of the invention, the expression "functionalized chain" means, for example, an alkyl chain comprising at least one functional (reactive) group chosen, for example, from those recited above. For example, in one embodiment, the hydrogen atoms of at least one alkyl chain may be substituted at least partially with fluorine atoms.

According to the invention, these chains may be linked directly to the polymer skeleton or via an ester function or a perfluoro group.

For the purposes of the invention, the term "polymer" means a compound containing at least 2 repeating units, such as, for example, a compound containing at least 3 repeating units, which may be identical.

As used herein, the expression "hydrocarbon-based repeating unit" includes a repeating unit comprising from 2 to 80 carbon atoms, such as, for example, from 2 to 60 carbon atoms. The at least one hydrocarbon-based repeating unit may also comprise oxygen atoms. The hydrocarbon-based repeating unit may be chosen from saturated and unsaturated hydrocarbon-based repeating units which in turn may be chosen from linear hydrocarbon-based repeating units, branched hydrocarbon-based repeating units and cyclic hydrocarbon-based repeating units. The at least one hydrocarbon-based repeating unit may comprise, for example, at least one hetero atom that is part of the polymer skeleton, i.e., not pendant. The at least one hetero atom may be chosen, for example, from nitrogen, sulphur, and phosphorus. For example, the at least one hetero atom may be a nitrogen atom, such as a non-pendant nitrogen atom. In another embodiment, the at least one hydrocarbon-based repeating unit may comprise at least one hetero atom with the proviso that the at least one hetero atom is not nitrogen. In another embodiment, the at least one hetero atom is combined with at least one atom chosen from oxygen and carbon to form a hetero atom group. In one embodiment, the hetero atom group comprises a carbonyl group.

The at least one repeating unit comprising at least one hetero atom may be chosen, for example, from amide groups, carbamate groups, and urea groups. In one embodiment, the at least one repeating unit comprises amide groups forming a polyamide skeleton. In another embodiment, the at least one repeating unit comprises carbamate groups and/or urea groups forming a polyurethane skeleton, a polyurea skeleton and/or a polyurethane-polyurea skeleton. The pendant chains, for example, can be linked directly to at least one of the hetero atoms of the polymer skeleton. In yet another embodiment, the at least one hydrocarbon-based repeating unit may comprise at least one hetero atom group with the proviso that the at least one hetero atom group is not an amide group. In one embodiment, the polymer skeleton comprises at least one repeating unit chosen from silicone units and oxyalkylene units, the at least one repeating unit being between the hydrocarbon-based repeating units.

In one embodiment, the composition of the invention comprises at least one structuring polymer with nitrogen atoms, such as amide, urea, or carbamate units, such as amide units, and at least one polar oil.

In one embodiment, in the at least one structuring polymer, the percentage of the total number of fatty chains ranges from 40% to 98% relative to the total number of repeating units and fatty chains, and as a further example, from 50% to 95%. In a further embodiment wherein the polymer skeleton is a polyamide skeleton, in the at least one structuring polymer, the percentage of the total number of fatty chains ranges from 40% to 98% relative to the total number of all amide units and fatty chains, and as a further example, from 50% to 95%.

In a further embodiment, the nature and proportion of the at least one hydrocarbon-based repeating unit comprising at least one hetero atom depends on the nature of a liquid fatty phase of the composition and is, for example, similar to the nature of the fatty phase. For example, not to be limited as to theory, the more polar the hydrocarbon-based repeating units containing a hetero atom, and in high proportion, which corresponds to the presence of several hetero atoms, the greater the affinity of the at least one structuring polymer to polar oils. Conversely, the more non-polar, or even apolar, and lesser in proportion the hydrocarbon-based repeating units containing a hetero atom, the greater the affinity of the polymer for apolar oils.

In another embodiment, the invention is drawn to a structured composition containing at least one liquid fatty phase structured with at least one structuring polymer, wherein said at least one structuring polymer is a polyamide comprising a polymer skeleton comprising at least one amide repeating unit and optionally at least one pendant fatty chain and/or at least one terminal chain that are optionally functionalized and comprising at least one chain chosen from alkyl and alkenyl chains, such as alkyl and alkenyl chains comprising at least 4 carbons atoms, and further such as alkyl and alkeny chains comprising from 8 to 120 carbon atoms, bonded to at least one of the amide repeating units via at least one linking group. The liquid fatty phase further contains at least one inert filler for thickening the liquid fatty phase. The at least one liquid fatty phase, the at least one structuring polyamide and the at least one inert filler together form a physiologically acceptable medium.

When the structuring polymer has amide repeating units, the pendant fatty chains may be linked to at least one of the nitrogen atoms in the amide repeating units.

The structuring polymer, for example the polyamide polymer, may have a weight-average molecular mass of less than 100,000, such as less than 50,000. In another embodiment, the weight-average molecular mass may range from 1000 to 30,000, such as from 2000 to 20,000, further such as from 2000 to 10,000.

The structuring polymer, as form example the polyamide polymer, is non soluble in water or in aqueous phase. In another embodiment the structuring polymer has non ionic group.

As discussed, the at least one structuring polymer may, for example, be chosen from polyamide polymers. A polyamide polymer may comprise, for example, a polymer skeleton which comprises at least one amide repeating unit, i.e., a polyamide skeleton. In one embodiment, the polyamide skeleton may further comprise at least one terminal fatty chain chosen from alkyl chains, for example, alkyl chains comprising at least four carbon atoms, and alkenyl chains, for example, alkenyl chains comprising at least four carbon atoms, bonded to the at least one polyamide skeleton via at least one linking group, and/or at least one pendant fatty chain chosen from alkyl chains, for example, alkyl chains comprising at least four carbon atoms, and alkenyl chains, for example, alkenyl chains comprising at least four carbon atoms, bonded to the at least one polyamide skeleton via at least one linking group. In one embodiment, the polyamide skeleton may comprise at least one terminal fatty chain chosen from fatty chains comprising 8 to 120 carbon atoms, such as, for example, 12 to 68 carbon atoms, bonded to the at least one polyamide skeleton via at least one linking group and/or at least one pendant fatty chain chosen from fatty chains comprising 8 to 120 carbon atoms, such as, for example, 12 to 68 carbon atoms, bonded to the at least one polyamide skeleton via at least one linking group, such as bonded to any carbon or nitrogen of the polyamide skeleton via said at least one linking group. In one embodiment, the at least one linking group is chosen from single bonds and urea, urethane, thiourea, thiourethane, thioether, thioester, ester, ether and amine groups. In another embodiment, the linking groups are chosen from ureas, esters, and amines, and as a further example, from esters and amines. The bond is, for example, an ester bond. In one embodiment, these polymers comprise a fatty chain at each end of the polymer skeleton, such as the polyamide skeleton.

In one embodiment, due to the presence of at least one chain, the polyamide polymers may be readily soluble in oils (i.e., water-immiscible liquid compounds) and thus may give macroscopically homogeneous compositions even with a high content (at least 25%) of the polyamide polymers, unlike certain polymers of the prior art that do not contain such alkyl or alkenyl chains at the end of the polyamide skeleton. As defined herein, a composition is soluble if it has a solubility of greater than 0.01 g per 100 ml of solution at 25° C.

In a further embodiment, the polyamide polymers can be chosen from polymers resulting from at least one polycondensation reaction between at least one acid chosen from dicarboxylic acids comprising at least 32 carbon atoms, such as 32 to 44 carbon atoms, and at least one amine chosen from diamines comprising at least 2 carbon atoms, such as from 2 to 36 carbon atoms, and triamines comprising at least 2 carbon atoms, such as from 2 to 36 carbon atoms. The at least one dicarboxylic acid can, for example, be chosen from dimers of at least one fatty acid comprising at least 16 carbon atoms, such as oleic acid, linoleic acid and linolenic acid. The at least one amine can, for example, be chosen from diamines, such as ethylenediamine, hexylenediamine, hexamethylenediamine, phenylenediamine and triamines, such as ethylenetriamine.

The polyamide polymers may also be chosen from polymers comprising at least one terminal carboxylic acid group. The at least one terminal carboxylic acid group can, for example, be esterified with at least one alcohol chosen from monoalcohols comprising at least 4 carbon atoms. For example, the at least one alcohol can be chosen from monoalcohols comprising from 10 to 36 carbon atoms. In a further embodiment, the monoalcohols can comprise from 12 to 24 carbon atoms, such as from 16 to 24 carbon atoms, and for example 18 carbon atoms.

In one embodiment, the at least one polyamide polymer may be chosen from those described in U.S. Pat. No. 5,783,657, the disclosure of which is incorporated herein by reference, which are polyamide polymers of formula (I):

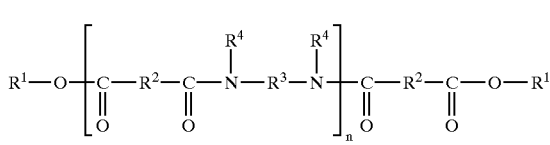

(I)

in which:
n is an integer which represents the number of amide units such that the number of ester groups present in said at least one polyamide polymer ranges from 10% to 50% of the total number of all said ester groups and all said amide groups comprised in the at least one polyamide polymer;

$R^1$, which are identical or different, are each chosen from alkyl groups comprising at least 4 carbon atoms and alkenyl groups comprising at least 4 carbon atoms. In one embodiment, the alkyl group comprises from 4 to 24 carbon atoms and the alkenyl group comprises from 4 to 24 carbon atoms;

$R^2$, which are identical or different, are each chosen from $C_4$ to $C_{42}$ hydrocarbon-based groups with the proviso that at least 50% of all $R^2$ are chosen from $C_{30}$ to $C_{42}$ hydrocarbon-based groups;

$R^3$, which are identical or different, are each chosen from organic groups comprising atoms chosen from carbon atoms, hydrogen atoms, oxygen atoms and nitrogen atoms with the proviso that $R^3$ comprises at least 2 carbon atoms; and $R^4$, which are identical or different, are each chosen from hydrogen atoms, $C_1$ to $C_{10}$ alkyl groups and a direct bond to at least one group chosen from $R^3$ and another $R^4$ such that when said at least one group is chosen from another $R^4$, the nitrogen atom to which both $R^3$ and $R^4$ are bonded forms part of a heterocyclic structure defined in part by $R^4$—N—$R^3$, with the proviso that at least 50% of all $R^4$ are chosen from hydrogen atoms.

In the polymer of formula (I), the terminal fatty chains that are optionally functionalized for the purposes of the invention are terminal chains linked to the last hetero atom, in this case nitrogen, of the polyamide skeleton.

In one embodiment, the ester groups of formula (I), which form part of the terminal and/or pendant fatty chains for the purposes of the invention, are present in an amount ranging from 15% to 40% of the total number of ester and amide groups (i.e. hetero atom groups), such as from 20% to 35%.

In formula (I), in one embodiment, n may be an integer ranging from 1 to 10, from example from 1 to 5, and as further for example an integer ranging from 3 to 5. In the present invention, $R^1$, which are identical or different, can, for example, each be chosen from C12 to $C_{22}$ alkyl groups, such as from $C_{16}$ to $C_{22}$ alkyl groups.

In the present invention, $R^2$, which are identical or different, can, for example, each be chosen from $C_{10}$ to $C_{42}$ hydrocarbon-based, e.g., alkylene groups. At least 50% of all $R^2$, for example at least 75% of all $R^2$, which are identical or different, can, for example, each be chosen from groups comprising from 30 to 42 carbon atoms. In the two aforementioned embodiments, the remaining $R^2$, which are identical or different, can, for example, each be chosen from $C_4$ to $C_{18}$ groups, such as $C_4$ to $C_{12}$ groups.

$R^3$, which can be identical or different, can, for example, each be chosen from $C_2$ to $C_{36}$ hydrocarbon-based groups and polyoxyalkylene groups. In another example, $R^3$, which can be identical or different, can each, for example, be chosen from $C_2$ to $C_{12}$ hydrocarbon-based groups. In another embodiment, $R^4$, which can be identical or different, can each be chosen from hydrogen atoms.

As used herein, hydrocarbon-based groups may be chosen from linear, cyclic and branched, and saturated and unsaturated groups. The hydrocarbon-based groups can be chosen from aliphatic and aromatic groups. In one example, the hydrocarbon-based groups are chosen from aliphatic groups. The alkyl and alkylene groups may be chosen from linear, cyclic and branched, and saturated and unsaturated groups.

In general, the pendant and terminal fatty chains may be chosen from linear, cyclic and branched, and saturated and unsaturated groups. The pendant and terminal fatty chains can be chosen from aliphatic and aromatic groups. In one example, the pendant and terminal fatty chains are chosen from aliphatic groups.

According to the invention, the structuring of the liquid fatty phase is obtained with the aid of at least one structuring polymer, such as the at least one polymer of formula (I). The at least one polyamide polymer of formula (I) may, for example, be in the form of a mixture of polymers, and this mixture may also comprise a compound of formula (I) wherein n is equal to zero, i.e., a diester.

Non-limiting examples of an at least one polyamide polymer which may be used in the composition according to the present invention include the commercial products sold or made by Arizona Chemical under the names Uniclear 80 and Uniclear 100. These are sold, respectively, in the form of an 80% (in terms of active material) gel in a mineral oil and a 100% (in terms of active material) gel. These polymers have a softening point ranging from 88° C. to 94° C., and may be mixtures of copolymers derived from monomers of (i) $C_{36}$ diacids and (ii) ethylenediamine, and have a weight-average molecular mass of about 6000. Terminal ester groups result from esterification of the remaining acid end groups with at least one alcohol chosen from cetyl alcohol and stearyl alcohol. A mixture of cetyl and stearyl alcohols is sometimes called cetylstearyl alcohol.

Other non-limiting examples of an at least one polyamide polymer which may be used in the composition according to the present invention include polyamide polymers (or polyamide resins) resulting from the condensation of at least one aliphatic dicarboxylic acid and at least one diamine, the carbonyl and amine groups being condensed via an amide bond. In one embodiment, these polymers contain more than two carbonyl groups and more than two amine groups. Examples of these polyamide polymers are those sold or made under the brand name Versamid by the companies General Mills Inc. and Henkel Corp. (Versamid 930, 744 or 1655) or by the company Olin Mathieson Chemical Corp. under the brand name Onamid, in particular Onamid S or C. These resins have a weight-average molecular mass ranging from 6000 to 9000. For further information regarding these polyamides, reference may be made to U.S. Pat. Nos. 3,645,705 and 3,148,125, the disclosures of which are hereby incorporated by reference. In one embodiment, Versamid 930 or 744 may be used.

Other examples of polyamides include those sold or made by the company Arizona Chemical under the references Uni-Rez (2658, 2931, 2970, 2621, 2613, 2624, 2665, 1554, 2623 and 2662) and the product sold or made under the reference Macromelt 6212 by the company Henkel. For further information regarding these polyamides, reference may be made to U.S. Pat. No. 5,500,209, the disclosure of which is hereby incorporated by reference. Such polyamides display high melt viscosity characteristics.

MACROMELT 6212, for example, has a high melt viscosity at 190° C. of 30–40 poise (as measured by a Brookfield Viscometer, Model RVF #3 spindle, 20 RPM).

In a further embodiment, the at least one polyamide polymer may be chosen from polyamide resins from vegetable sources. Polyamide resins from vegetable sources may be chosen from, for example, the polyamide resins of U.S. Pat. Nos. 5,783,657 and 5,998,570, the disclosures of which are herein incorporated by reference.

The at least one structuring polymer in the compositions of the invention may have a softening point greater than 50° C., such as from 65° C. to 190° C., preferably less than 150° C. and further such as from 70° C. to 130° C., and even further such as from 80° C. to 105° C. This softening point may be lower than that of structuring polymers used in the art which may facilitate the use of the at least one structuring polymer of the present invention and may limit the degradation of the liquid fatty phase. These polymers may be non waxy polymers. The softening point can be measured by a well known method as Differential Scanning Calorimetry (i.e. DSC method) with a temperature rise of 5 to 10° C./min.

In one embodiment, the at least one structuring polymer in the composition according to the invention corresponds to the polyamide polymers of formula (I). Due to fatty chain(s), these polymers may be readily soluble in oils and thus lead to compositions that are macroscopically homogeneous even with a high content (at least 25%) of at least one structuring polymer, unlike polymers not containing a fatty chain.

The at least one structuring polymer may be present in the composition in an amount ranging, for example, from 0.5% to 80% by weight relative to the total weight of the composition, such as for example 2% to 60%, and further, for example, from 5 to 40%. In a further embodiment the at least one structuring polymer may be present in the composition in an amount ranging, for example, from 5% to 25% by weight relative to the total weight of the composition.

In one embodiment, when the at least one structuring polymer of the present invention comprises a urea urethane having the following formula:

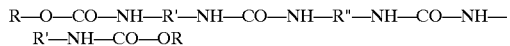
R—O—CO—NH—R'—NH—CO—NH—R"—NH—CO—NH—R'—NH—CO—OR then R represents $C_nH_{2n+1}$, wherein n represents an integer having a value greater than 22, for example from 23 to 120, and further, for example from 23 to 68, or $C_mH_{2m+1}(OC_pH_{2p})_r$—, wherein m represents an integer having a value of greater than 18, for example from 19 to 120, and further, for example, from 23 to 68, p represents an integer having a value of from 2 to 4, and r represents an integer having a value of from 1 to 10,

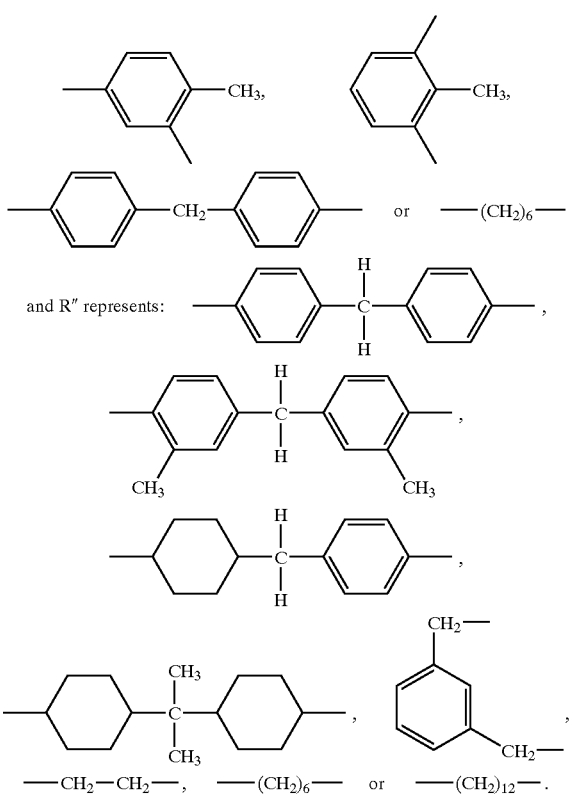

and R" represents: (structures shown)

—CH$_2$—CH$_2$—, —(CH$_2$)$_6$— or —(CH$_2$)$_{12}$—.

In another embodiment of the invention, the present invention is drawn to a structured composition comprising at least one liquid fatty phase structured with at least one structuring polymer comprising a polymer skeleton comprising at least one hydrocarbon-based repeating unit comprising at least one hetero atom, wherein the at least one structuring polymer further comprises at least one terminal fatty chain, optionally functionalized, chosen from alkyl and alkenyl chains, such as alkyl and alkenyl chains having at least four carbon atoms, and further such as alkyl and alkenyl chains comprising from 8 to 120 carbon atoms, bonded to the polymer skeleton via at least one linking group chosen from amides, ureas, and esters, wherein when said at least one linking group is chosen from esters, said at least one terminal fatty chain is chosen from branched alkyl groups. The at least one structuring polymer may also comprise at least one pendant fatty chain, optionally functionalized, chosen from alkyl and alkenyl chains, such as alkyl and alkenyl chains having at least four carbon atoms, and further such as alkyl and alkenyl chains comprising from 8 to 120 carbon atoms, bonded to any carbon or hetero atom of the polymer skeleton via at least one linking group chosen from amides, ureas, and esters, wherein when said at least one linking group is chosen from esters, said at least one terminal fatty chain is chosen from branched alkyl groups. The at least one structuring polymer may comprise both at least one pendant fatty chain and at least one terminal fatty chain as defined above in this paragraph.

Further, an embodiment of the invention relates to a skin, lip, or keratinous fiber care or make-up composition comprising a structured composition containing at least one liquid fatty phase structured with at least one structuring polymer comprising a polymer skeleton comprising at least one hydrocarbon-based repeating unit comprising at least one hetero atom and at least one inert filler.

Additionally, an embodiment of the invention relates to a skin, lip, or keratinous fiber care or make-up composition comprising a structured composition containing at least one liquid fatty phase structured with at least one structuring polymer comprising a polymer skeleton comprising at least one hydrocarbon-based repeating unit comprising at least one hetero atom, at least one inert filler, and at least one coloring agent.

Additionally, an embodiment of the invention relates to a method of making up skin, lips or keratinous fibers or caring for skin, lips keratinous fibers or treating skin, lips or keratinous fibers comprising applying to said skin, lips, or keratinous fibers a structured composition containing at least one liquid fatty phase structured with at least one structuring polymer comprising a polymer skeleton comprising at least one hydrocarbon-based repeating unit comprising at least one hetero atom and at least one inert filler.

Inert Filler

According to the invention, the composition contains at least one inert filler. The term "filler" means any particle that is solid at room temperature and atmospheric pressure, used alone or in combination, which does not react chemically with the various ingredients of the composition and which is insoluble in these ingredients, even when these ingredients are raised to a temperature above room temperature and in particular to their softening point or their melting point.

The at least one inert filler has a melting point at least greater than 150° C., for example greater than 170° C. and further as for example, greater than 200° C. The at least one inert filler may or may not be absorbent, i.e., capable in particular of absorbing the oils of the composition and also the biological substances secreted by the skin. The absorbent fillers often have the property of making the deposit of composition on the keratin materials matte, which is particularly desired for a foundation and a concealer product. In one embodiment, the at least one inert filler may have an apparent diameter ranging from 0.01 $\mu$m to 150 $\mu$m, such as from 0.5 $\mu$m to 120 $\mu$m, for example from 1 $\mu$m to 80 $\mu$m. An apparent diameter corresponds to the diameter of the circle into which the elementary particle fits along its shortest dimension (thickness for leaflets).

The at least one inert filler may be present in the inventive composition in an amount ranging from 0.1% to 40% relative to the weight of the total composition, such as from 2% to 30%, and, for example, from 5% to 20%.

The at least one inert filler may be mineral or organic, and lamellar, spherical or oblong. The at least one inert filler may be chosen from talc, mica, silica, kaolin, polyamide powders such as Nylon® (Orgasol® from Atochem) powder, poly-β-alanine powder, polyethylene powder, acrylic polymer powder and in particular polymethyl methacrylate (PMMA) powder, for instance the product sold or made by Wacker under the reference Covabead LH-85 (particle size 10–12 $\mu$m) or acrylic acid copolymer powder (Polytrap® from Dow Corning), polytetrafluoroethylene (Teflon®) powders, lauroyllysine, boron nitride, starch, hollow polymer microspheres such as those of polyvinylidene chloride/acrylonitrile, for instance Expancel® (Nobel Industrie), hollow polymer microspheres (Tospearl® from Toshiba, for example), precipitated calcium carbonate, magnesium carbonate and hydrocarbonate, hydroxyapatite, hollow silica microspheres (Silica Beads® from Maprecos), glass or ceramic microcapsules and polyester particles. The at least one inert filler may be surface-treated, e.g., to make them lipophilic.

The at least one inert filler may be porous so as to absorb the sweat and/or sebum secreted by the skin. Such inert fillers include silica, polyethylene powder, polyamide (Nylon®) powder, kaolin, starch derivatives and Polytrap®.

In order to minimize the exudation of the composition in cast form, the at least one inert filler used in the composition may contain a chemical group of the same chemical nature as those of the units of the structuring polymer or a chemical group capable of forming physical bonds of the same type as that of the units of the polymer (for example, chosen from self-complementary hydrogen bonds, $\pi$ interactions between unsaturated rings or filler-transfer interactions, dipolar interactions, and coordination bonds with organometallic derivatives). Thus, for structuring polymers containing units of the amide, urea and/or urethane type, the at least one inert filler used may contain groups capable of forming hydrogen bonds, like these structuring polymers. As fillers capable of forming hydrogen bonds, mention may be made of fillers or particles of acrylic polymer such as PMMA for instance the product sold by Wacker under the reference Covabead LH-85 (particle size 10–12 $\mu$m) and Polytrap® sold or made by Dow Corning, hydrophobic-treated silica, polyamide (Nylon®) powders (Orgasol® from Atochem), and mixtures thereof. For units of the ester type, the fillers used may be of the polyester type.

The surface of the silica may be chemically modified, by hydrophobic chemical treatments, giving rise to a decrease in the number of silanol groups. The hydrophobic groups may be:

trimethylsiloxyl groups, which are obtained, for example, by treating fumed silica in the presence of hexamethyldisilazane. Silicas thus treated are known as "silica silylate" according to the CTFA (6th edition, 1995). They are sold, or made for example, under the references "Aerosil R812®" by the company Degussa and "CAB-O-SIL TS-530®" by the company Cabot;

dimethylsilyloxyl or polydimethylsiloxane groups, which are obtained, for example, by treating fumed silica in the presence of polydimethylsiloxane or dimethyldichlorosilane. Silicas thus treated are known as "silica dimethyl silylate" according to the CTFA (6th edition, 1995). They are made or sold, for example, under the references "Aerosil R972®" and "Aerosil R974®" by the company Degussa, and "CAB-O-SIL TS-610®" and "CAB-O-SIL TS-720®" by the company Cabot;

groups derived from reacting fumed silica with silane alkoxides or siloxanes. These treated silicas are, for example, the products made or sold under the reference "Aerosil R805®" by the company Degussa.

According to the invention, a hydrophobic silica, such as a fumed silica, may be used as lipophilic gelling agent or rheological agent. The use of fumed silica may make it possible to obtain a translucent or even transparent composition, in particular in the form of a stick which does not exude, in the absence of opacifying particles such as waxes, fillers and pigments (including nacres).

In one embodiment, the filler is lipophilic or traited to be lipophilic.

Amphiphilic Compound

The at least one structuring polymer and the at least one inert filler can be combined with at least one amphiphilic compound that is liquid and non-volatile at room temperature and has a hydrophilic/lipophilic balance (HLB) value of less than 12, for example ranging from 1 to 8 or from 1 to 5. These amphiphilic compounds may act to reinforce the structuring properties of the polymer containing at least one hetero atom, to facilitate the implementation of the polymer and to improve the ability of the stick to be deposited. However, it is possible to obtain a stick with good mechanical and/or thermal properties without including at least one amphiphilic compound.

Depending on the intended application, such as a stick, hardness of the composition may also be considered. The hardness of a composition may, for example, be expressed in gramforce (gf). The composition of the present invention may, for example, have a hardness ranging from 20 gf to 2000 gf, such as from 20 gf to 900 gf, and further such as from 20 gf to 600 gf.

This hardness is measured in one of two ways. A first test for hardness is according to a method of penetrating a probe into said composition and in particular using a texture analyzer (for example TA-XT2i from Rheo) equipped with an ebonite cylinder of height 25 mm and diameter 8 mm. The hardness measurement is carried out at 20° C. at the center of 5 samples of said composition. The cylinder is introduced into each sample of composition at a pre-speed of 2 mm/s and then at a speed of 0.5 mm/s and finally at a post-speed of 2 mm/s, the total displacement being 1 mm. The recorded hardness value is that of the maximum peak observed. The measurement error is ±50 gf.

The second test for hardness is the "cheese wire" method, which involves cutting an 8.1 mm or preferably 12.7 mm in diameter stick of composition and measuring its hardness at 20° C. using a DFGHS 2 tensile testing machine from Indelco-Chatillon Co. at a speed of 100 mm/minute. The hardness value from this method is expressed in grams as the shear force required to cut a stick under the above conditions. According to this method, the hardness of compositions according to the present invention which may be in stick form may, for example, range from 30 gf to 300 gf, such as from 30 gf to 250 gf, and further such as from 30 gf to 200 gf.

The hardness of the composition of the present invention may be such that the compositions are self-supporting and can easily disintegrate to form a satisfactory deposit on a keratinous material. In addition, this hardness may impart good impact strength to the inventive compositions which may be molded or cast, for example, in stick or dish form. The composition of the invention may be a solid, in the form of molded or poured sticks.

The skilled artisan may choose to evaluate a composition using at least one of the tests for hardness outlined above based on the application envisaged and the hardness desired. If one obtains an acceptable hardness value, in view of the intended application, from at least one of these hardness tests, the composition falls within the scope of the invention.

As is evident, the hardness of the composition according to the invention may, for example, be such that the composition is advantageously self-supporting and can disintegrate easily to form a satisfactory deposit on the skin and/or the lips and/or superficial body growths, such as keratinous fibres. In addition, with this hardness, the composition of the invention may have good impact strength.

According to the invention, the composition in stick form may have the behavior of a deformable, flexible elastic solid, giving noteworthy elastic softness on application. The compositions in stick form of the prior art do not have these properties of elasticity and flexibility.

The at least one amphiphilic compound which can be used in the composition of the invention may, for example, comprise a lipophilic part linked to a polar part, the lipophilic part comprising a carbon-based chain containing at least 8 carbon atoms, for example from 18 to 32 carbon atoms or from 18 to 28 carbon atoms. The polar part of the at least one amphiphilic compound may, in one embodiment, be the residue of a compound chosen from alcohols and polyols containing from 1 to 12 hydroxyl groups, and polyoxyalkylenes comprising at least 2 oxyalkylene units and containing from 0 to 20 oxypropylene units and/or from 0 to 20 oxyethylene units. For example, the at least one amphiphilic compound may be an ester chosen from the hydroxystearates, oleates and isostearates of glycerol, of sorbitan and of methylglucose, and from branched $C_{12}$ to $C_{26}$ fatty alcohols such as octyldodecanol. Among these esters, monoesters and mixtures of mono- and diesters can also be used.

The respective contents of the at least one lipophilic inert filler, the at least one polymer containing a hetero atom and optionally that of at least one amphiphilic compound are chosen according to the desired hardness of the composition and as a function of the specific application envisaged. The respective amounts of polymer, of inert filler and of amphiphilic compound should be such that they produce a stick which can be worn down. In practice, the amount of the at least one polymer may be chosen from 0.5% to 80% of the total weight of the composition, for example from 2% to 60%, from 5% to 40%, and from 5% to 25%. The amount of at least one amphiphilic compound in practice, if it is present, may be chosen from 0.1% to 35% of the total weight of the composition, for example from 1% to 20% or from 1% to 15%.

The at least one structuring polymer has an affinity with the fatty phase and in particular with a chemical portion of one of the oils forming the liquid fatty phase of the composition so that physical links with the oils, such as hydrogen bonds, or as above-mentioned, are formed.

Liquid Fatty Phase

The at least one liquid fatty phase, in one embodiment, may comprise at least one oil. In one embodiment, at least one oil has an affinity with the structuring polymer. The at least one oil, for example, may be chosen from polar oils and apolar oils including hydrocarbon-based liquid oils and oily liquids at room temperature. In one embodiment, the composition of the invention comprises at least one structuring polymer and at least one polar oil. The polar oils of the invention, for example, may be added to the apolar oils, the apolar oils acting in particular as co-solvent for the polar oils.

According to the invention, the structuring of the at least one liquid fatty phase may be obtained with the aid of at least one structuring polymer, such as the polymer of formula (I). In general, the polymers of formula (I) may be in the form of mixtures of polymers, these mixtures also possibly containing a synthetic product corresponding to a compound of formula (I) in which n is 0, i.e., a diester.

The liquid fatty phase of the composition may contain more than 30%, for example, more than 40%, of liquid oil(s) having a chemical nature close to the chemical nature of the skeleton (hydrocarbon or silicone based) of the structuring polymer, and for example from 50% to 100%. In one embodiment, the liquid fatty phase structured with a polyamide-type skeleton, or polyurea, or polyurethane, or polyurea-urethane-type skeleton contains a high quantity, i.e., greater than 30%, for example greater than 40% relative to the total weight of the liquid fatty phase, or from 50% to 100%, of at least one apolar, such as hydrocarbon-based, oil. For the purposes of the invention, the expression "hydrocarbon-based oil" means an oil comprising carbon and hydrogen atoms, optionally with at least one group chosen from hydroxyl, ester, carboxyl and ether groups.

For a liquid fatty phase structured with a polymer containing a partially silicone-based skeleton, this fatty phase may contain more than 30%, for example, more than 40%, relative to the total weight of the liquid fatty phase and, for example, from 50% to 100%, of at least one silicone-based liquid oil, relative to the total weight of the liquid fatty phase.

For a liquid fatty phase structured with an apolar polymer of the hydrocarbon-based type, this fatty phase may contain more than 30%, for example more than 40% by weight, and, as a further example, from 50% to 100% by weight, of at least one liquid apolar, such as hydrocarbon-based, oil, relative to the total weight of the liquid fatty phase.

For example, the at least one polar oil useful in the invention may be chosen from:

hydrocarbon-based plant oils with a high content of triglycerides comprising fatty acid esters of glycerol in which the fatty acids may have varied chain lengths from $C_4$ to $C_{24}$, these chains possibly being chosen from linear and branched, and saturated and unsaturated chains; these oils can be chosen from, for example, wheat germ oil, corn oil, sunflower oil, karite butter, castor oil, sweet almond oil, macadamia oil, apricot oil, soybean oil, cotton oil, alfalfa oil, poppy oil, pumpkin oil, sesame oil, marrow oil, rapeseed oil, avocado oil, hazelnut oil, grape seed oil, blackcurrant seed oil, evening primrose oil, millet oil, barley oil, quinoa oil, olive oil, rye oil, safflower oil, candlenut oil, passion flower oil and musk rose oil; or alternatively caprylic/capric acid triglycerides such as those sold by Stearineries Dubois or those sold under the names Miglyol 810, 812 and 818 by Dynamit Nobel;

synthetic oils or esters of formula $R_5COOR_6$ in which $R_5$ is chosen from linear and branched fatty acid residues containing from 1 to 40 carbon atoms and $R_6$ is chosen from, for example, a hydrocarbon-based chain containing from 1 to 40 carbon atoms, on condition that $R_5+R_6 \geq 10$, such as, for example, purcellin oil (cetostearyl octanoate), isononyl isononanoate, $C_{12}$–$C_{15}$ alkyl benzoates, isopropyl myristate, 2-ethylhexyl palmitate, isostearyl isostearate and alkyl or polyalkyl octanoates, decanoates or ricinoleates; hydroxylated esters such as isostearyl lactate and diisostearyl malate; and pentaerythritol esters;

synthetic ethers containing from 10 to 40 carbon atoms;

$C_8$ to $C_{26}$ fatty alcohols such as oleyl alcohol; and $C_8$ to $C_{26}$ fatty acids such as oleic acid, linolenic acid or linoleic acid.

The at least one apolar oil according to the invention is chosen from, for example, silicone oils chosen from volatile and non-volatile, linear and cyclic polydimethylsiloxanes (PDMSs) that are liquid at room temperature; polydimethylsiloxanes comprising alkyl or alkoxy groups which are pendant and/or at the end of the silicone chain, the groups each containing from 2 to 24 carbon atoms; phenylsilicones such as phenyl trimethicones, phenyl dimethicones, phenyl trimethylsiloxy diphenylsiloxanes, diphenyl dimethicones, diphenyl methyldiphenyl trisiloxanes and 2-phenylethyl trimethylsiloxysilicates; hydrocarbons chosen from linear and branched, volatile and non-volatile hydrocarbons of synthetic and mineral origin, such as volatile liquid paraffins (such as isoparaffins and isododecane) or non-volatile liquid paraffins and derivatives thereof, liquid petrolatum, liquid lanolin, polydecenes, hydrogenated polyisobutene such as hydrogenated polybutene, e.g. Parleam®, from Nippon Oil Fats and squalane; and mixtures thereof. The structured oils, for example those structured with polyamides such as those of formula (I) or with polyurethanes, polyureas, polyurea-urethanes, in accordance with the invention, may be, in one embodiment, apolar oils, such as an oil or a mixture of hydrocarbon oils chosen from those of mineral and synthetic origin, chosen from hydrocarbons such as alkanes such as Parleam® oil, isoparaffins including isododecane, and squalane, and mixtures thereof. These oils may, in one embodiment, be combined with at least one phenylsilicone oil.

The liquid fatty phase, in one embodiment, contains at least one non-volatile oil chosen from, for example, hydrocarbon-based oils of mineral, plant and synthetic origin, synthetic esters or ethers, silicone oils and mixtures thereof.

For the purposes of the invention, the expression "volatile solvent or oil" means any non-aqueous medium capable of evaporating on contact with the skin or the lips in less than one hour at room temperature and atmospheric pressure. The volatile solvent(s) of the invention is(are) organic solvents, such as volatile cosmetic oils that are liquid at room temperature, having a non-zero vapor pressure, at room temperature and atmospheric pressure, ranging in particular from $10^{-2}$ to 300 mmHg (1.3 to 40 000 Pa) and, for example, greater than 0.03 mmHg (4 Pa) and further example greater than 0.3 mmHg (40 Pa). The expression "non-volatile oil" means an oil which remains on the skin or the lips at room temperature and atmospheric pressure for at least several hours, such as those having a vapor pressure of less than $10^{-2}$ mmHg (1.3 Pa).

According to the invention, these volatile solvents (or oils) may facilitate the staying power or long wearing properties over time and also the transfer-resistance properties of the composition on the skin, the lips or superficial body growths such as nails and keratinous fibers. Thus, the composition may contain at least one volatile solvent, such as at least one volatile oil. This at least one volatile solvent can be chosen from hydrocarbon-based solvents, silicone solvents optionally comprising alkyl or alkoxy groups that are pendent or at the end of a silicone chain, fluoro solvents, and mixtures thereof. The transfer-resistance properties are the ability of a deposit of the composition on the skin, the lips or superficial body growths not to become deposited onto a support placed in contact with the said deposit. These transfer-resistance properties are particularly advantageous when the composition contains coloring agents, which is especially the case for make-up compositions.

As volatile PDMSs which can be used in the invention, mention may be made of linear or cyclic silicone oils having a viscosity at room temperature of less than 8 cSt and containing, for example, from 2 to 7 silicon atoms, these silicones optionally comprising alkyl or alkoxy groups comprising from 1 to 10 carbon atoms. Volatile silicone oils that can be used in the invention may be chosen from octamethylcyclotetrasiloxane, decamethylcyclopentasiloxane, dodecamethylcyclohexasiloxane, heptamethylhexyltrisiloxane, heptamethyloctyltrisiloxane, hexamethyldisiloxane, octamethyltrisiloxane, decamethyltetrasiloxane and dodecamethylpentasiloxane, and mixtures thereof.

As volatile hydrocarbons which can be used in the invention, mention may be made of hydrocarbons comprising from 8 to 16 carbon atoms, and mixtures thereof, for example branched $C_8$–$C_{16}$ alkanes such as $C_8$–$C_{16}$ isoalkanes (also known as isoparaffins), for instance of petroleum origin, isododecane, isodecane, isohexadecane and, for example, the oils sold under the trade names Isopars or Permetyls, and mixtures thereof. $C_8$–$C_{16}$ branched esters such as isohexyl neopentanoate and mixtures thereof can also be used. The at least one volatile oil may be, in one embodiment, chosen from hydrocarbons comprising from 8 to 16 carbon atoms.

The at least one volatile solvent may represent a mass content up to 97.5% relative to the total weight of the composition, such as from 1% to 75% or 10% to 60%, for example from 20% to 60%. In general, the at least one volatile solvent should be present in an amount that is sufficient to obtain transfer-resistance properties and should be adapted by a person skilled in the art as a function of the desired intensity for these transfer-resistance properties.

This amount can be also adapted by a person skilled in the art according to the desired staying power or long wearing properties.

The at least one liquid fatty phase of the composition of the invention may further comprises a dispersion of lipid vesicles. The composition of the invention may also, for example, be in the form of a fluid anhydrous gel, a rigid anhydrous gel, a fluid simple emulsion, a fluid multiple emulsion, a rigid simple emulsion or a rigid multiple emulsion. The simple emulsion or multiple emulsion may comprise a continuous phase chosen from an aqueous phase optionally containing dispersed lipid vesicles, or a fatty phase optionally containing dispersed lipid vesicles. In one embodiment, the composition has a continuous oily phase or fatty phase and is more specifically an anhydrous composition, for example, a stick or dish form. An anhydrous composition is one that has less than 10% water by weight, such as, for example, less than 5% by weight.

Additional Additives

The composition of the invention can also comprise any additional additive usually used in the field under consideration, such as cosmetics or dermatology, chosen, for example, from antioxidants, essential oils, preserving agents, fragrances, waxes, fatty compounds that are pasty or viscous at room temperature, neutralizing agents, gums, liposoluble or lipodispersible gelling agents, liposoluble polymers or polymers that are dispersible in the medium, cosmetic or dermatological active agents such as, for example, emollients, moisturizers, vitamins, essential fatty acids, dispersants such as poly(12-hydroxystearic acid), coloring agents and mixtures thereof. These additives, if present, may each be present in the composition in a proportion of up to 20%, for example from 0.01% to 20%, and, as a further example, from 0.01% to 10% relative to the total weight of the composition.

The composition of the invention can also contain, as an additional additive, an aqueous phase containing water that is optionally thickened with an aqueous-phase thickener or gelled with a hydrophilic gelling agent and/or containing ingredients soluble in water and/or optionally water-miscible compounds. The water can represents from 0.01% to 70%. For a water-in-oil or oil-in-water emulsion, from 2% to 70% by weight of water, for example from 5% to 50% can be used.

Needless to say, a person skilled in the art will take care to select the optional additional additives and/or the amount thereof such that the advantageous properties of the composition according to the invention are not, or are not substantially, adversely affected by the envisaged addition.

The composition according to the invention can be in the form of a tinted or non tinted dermatological composition or care composition for keratin materials such as the skin, the lips and/or superficial body growths, such as keratinous fibers, in the form of an antisun composition or body hygiene composition, such as in the form of a deodorant product or make-up-removing product in stick form. It can be used, for example, as a care base for the skin, superficial body growths or the lips, for example, lip balms, for protecting the lips against cold and/or sunlight and/or the wind, or care cream for the skin, the nails or the hair.

The composition of the invention may also be in the form of a colored make-up product for the skin, such as a foundation, optionally having care or treating properties, a blusher, a face powder, an eyeshadow, a concealer product, an eyeliner, a make-up product for the body; a makeup product for the lips such as a lipstick, optionally having care or treating properties; a make-up product for superficial body growths such as the nails, the eyelashes, for example in the form of a mascara cake, or for the eyebrows and the hair, for example in the form of a pencil.

Needless to say, the composition of the invention should be cosmetically or dermatologically acceptable, i.e., it should contain a non-toxic physiologically acceptable medium and should be able to be applied to the skin, superficial body growths or the lips of human beings. For the purposes of the invention, the expression "cosmetically acceptable" means a composition of pleasant appearance, odour, feel and taste.

The composition may also contain at least one cosmetic active agent and/or at least one dermatological active agent, i.e., an agent having a beneficial effect on the skin, lips or body growths, and/or at least one coloring agent.

In one embodiment, the composition does not contain sensitizing agents, such as colophony.

Coloring agents

The coloring agent according to the invention may be chosen from the lipophilic dyes, hydrophilic dyes, pigments and nacreous pigments (i.e. nacres) usually used in cosmetic or dermatological compositions, and mixtures thereof. This coloring agent can generally be present in a proportion of from 0.01% to 50% relative to the total weight of the composition, for example from 0.5% to 40%, and, as a further example, from 5% to 30%, if it is present. In the case of a composition in the form of a free or compacted powder, the amount of coloring agent in the form of solid particles that are insoluble in the medium (nacres and/or pigments) may be up to 90% relative to the total weight of the composition.

The liposoluble dyes include, for example, Sudan Red, D&C Red 17, D&C Green 6, β-carotene, soybean oil, Sudan Brown, D&C Yellow 11, D&C Violet 2, D&C Orange 5, quinoline yellow and annatto. They can be present in an amount ranging from 0.1% to 20% of the weight of the composition, for example from 0.1% to 6% (if present). The water-soluble dyes are, for example, beetroot juice or methylene blue, and can represent up to 6% of the total weight of the composition.

The pigments may be white or colored, mineral and/or organic, and coated or uncoated and having a micron size or not. Among the mineral pigments which may be mentioned are titanium dioxide, optionally surface-treated, zirconium oxide, zinc oxide or cerium oxide, as well as iron oxide, chromium oxide, manganese violet, ultramarine blue, chromium hydrate and ferric blue. Among the organic pigments which may be mentioned are carbon black, pigments of D&C type, and lakes based on cochineal carmine or on barium, strontium, calcium or aluminium. The pigment(s) can be present in an amount ranging from 0.1% to 50%, for example from 0.5% to 40%, and, as a further example, from 2% to 30% relative to the total weight of the composition, if they are present.

The nacreous pigments may be chosen from white nacreous pigments such as mica coated with titanium or with bismuth oxychloride, colored nacreous pigments such as titanium mica with iron oxides, titanium mica with, for example, ferric blue or chromium oxide, titanium mica with an organic pigment of the type mentioned above, as well as nacreous pigments based on bismuth oxychloride or alternatively interferential or goniochromatic pigments. They can be present in an amount ranging from 0.1% to 20% relative to the total weight of the composition, for example from 0.1% to 15%, if they are present, and may or may not be surface-treated.

In one embodiment, the coloring agent are pigments (nacreous or not).

Waxes

The composition can optionally contain at least one wax to improve the structuring in stick form, although this rigid form can be obtained in the absence of wax. The composition may contain little or no wax, for example, less than 5% wax. The waxes useful in the composition are those mentioned previously.

Liposoluble or Dispersible Polymers

The composition of the invention may also contain at least one polymer that is liposoluble or dispersible in the medium, for example having an average molecular weight of from 500 to 1 000 000. In one embodiment, the at least one liposoluble or dispersible polymer may have an average molecular weight ranging from 1 to 500 000, for example from 5000 to 100 000 or from 5000 to 20 000. The at least one liposoluble or dispersible polymer may contribute towards increasing the viscosity and/or improving the staying power of the film. The at least one liposoluble or dispersible polymer may have a softening point of not more than 30° C.

As examples of liposoluble polymers which can be used in the invention, mention may be made of: polyalkylenes, such as polybutene, poly(meth)acrylates, alkylcelluloses with a linear or branched, saturated or unsaturated $C_1$ to $C_6$ alkyl radical, such as ethylcellulose and propylcellulose, silicone polymers that are compatible with the fatty phase, as well as vinylpyrrolidone (VP) copolymers, and mixtures thereof.

The at least one liposoluble or dispersible polymer in the composition of the invention may be used in an amount ranging from 0% to 20% (as active material) relative to the total weight of the composition, for example from 0.5% to 10%, if they are present.

Pasty fatty compound

The composition according to the invention may also contain at least one fatty compound that is pasty or viscous at room temperature. For the purposes of the invention, the expression "pasty fatty substance" means a fatty substance with a melting point ranging from 20° C. to 55° C., for example from 25° C. to 45° C., and from 25° C. to 40° C., and/or a viscosity at 40° C. ranging from 0.1 to 40 Pa.s (1 to 400 poises), for example from 0.5 to 25 Pa.s, measured using a Contraves TV or Rheomat 80 viscometer, equipped with a spindle rotating at 240 $min^{-1}$ for supplying with 60 Hz or at 200 $min^{-1}$ for supplying with 50 Hz. A person skilled in the art can select the spindle for measuring the viscosity from the spindles MS-r3 and MS-r4, on the basis of his general knowledge, so as to be able to carry out the measurement of the pasty compound tested.

According to the invention, at least one pasty fatty substance can be used. The at least one pasty fatty substance may be chosen from hydrocarbon-based compounds, optionally of polymeric type; it can also be chosen from silicone compounds and/or fluoro compounds; it may also be in the form of a mixture of hydrocarbon-based compounds and/or silicone compounds and/or fluoro compounds. In the case of a mixture of different pasty fatty substances, the hydrocarbon-based pasty compounds (containing mainly hydrogen and carbon atoms and optionally ester groups) may be used in major proportion.

Among the pasty compounds which may be used in the composition according to the invention, mention may be made of lanolins and lanolin derivatives such as acetylated lanolins or oxypropylenated lanolins or isopropyl lanolate, having a viscosity of from 18 to 21 Pa.s, for instance 19 to 20.5 Pa.s, and/or a melting point of from 30° C. to 55° C. and for example from 30° C. to 40° C., and mixtures thereof. It is also possible to use esters of fatty acids or of fatty alcohols, such as those containing from 20 to 65 carbon atoms (melting point of about from 20° C. to 35° C. and/or viscosity at 40° C. ranging from 0.1 to 40 Pa.s), such as triisostearyl citrate or cetyl citrate; arachidyl propionate; polyvinyl laurate; cholesterol esters, such as triglycerides of plant origin, such as hydrogenated plant oils (hydrogenated castor oil), viscous polyesters such as poly(12-hydroxystearic acid); polydimethylsiloxanes (PDMS) having alkyl or alkoxy pendant chains containing from 8 to 24 carbon atoms, and a melting point of 20–55° C. and form example form 20° C. to 40° C., such as stearyldimethicones (in particular DC2503 and DC25514 from Dow Corning); and mixtures thereof.

The at least one pasty fatty substance may be present in a proportion up to 60% by weight, relative to the total weight of the composition, for example from 0.5% to 45% by weight, and, as a further example, from 2% to 30% by weight, in the composition, if present.

The composition according to the invention may be manufactured by the known processes, that are generally used in cosmetics or dermatology. It may be manufactured by the process which comprises heating the polymer at least to its softening point, in adding the amphiphilic compound (s), the fillers and coloring agents and the additives thereto and then in mixing everything together until a clear, transparent solution is obtained. After reducing the temperature of the mixture obtained, the volatile solvent(s) is(are) then added. The homogeneous mixture obtained can then be cast in a suitable mold such as a lipstick mold or directly into the packaging articles (e.g., a case or dish).

Another embodiment of the invention is also a make-up composition in stick form containing at least one continuous liquid fatty phase structured with at least one non-waxy structuring polymer having a weight-average molecular mass of less than 100 000, and at least one inert filler; the at least one liquid fatty phase, the at least one structuring polymer and the at least one inert filler forming a physiologically acceptable medium. The at least one inert filler and the at least one non-waxy structuring polymer may be such that they give the composition the appearance of a deformable elastic solid with a hardness ranging from 30 to 300 gf, such as 30 to 250 gf, and further such as 30 to 200 gf, even in the absence of wax, as measured by the "cheese wire" method discussed above.

This make-up composition in stick form may contain at least one volatile solvent as defined above. The non-waxy polymer can, for example, be a polymer whose skeleton comprises hydrocarbon-based units containing a hetero atom, as defined above. For example, the non-waxy polymer can have a skeleton containing a polyamide group that may contain alkyl end groups linked to the skeleton via a linking group, such as of the ester type. An embodiment such as a lipstick, can contain, for example, at least one additive chosen from fatty compounds that are pasty at room temperature and waxes.

A subject of the invention is also a cosmetic care, make-up or treatment process for the keratin materials of human beings, such as the skin, the lips and superficial body growths, such as keratin materials, comprising the application to the keratin materials of the composition, for example the cosmetic composition, as defined above.

A subject of the invention is also the use of the combination of at least one structuring polymer having a weight-average molecular mass less than 100,000, such as less than 50,000, comprising a) a polymer skeleton comprising at least one hydrocarbon-based repeating unit comprising at least one hetero atom, and b) optionally at least one terminal fatty chain, optionally functionalized, comprising at least one chain chosen from alkyl and alkenyl chains, such as alkyl and alkenyl chains having at least 4 carbon atoms, and further such as alkyl and alkenyl chains having from 8 to 120 carbon atoms, bonded to the polymer skeleton via at least one linking group, and c) optionally at least one pendant fatty chain, optionally functionalized, comprising at least one chain chosen from alkyl and alkenyl chains, such as alkyl and alkenyl chains having at least 4 carbon atoms, and further such as alkyl and alkenyl chains having from 8 to 120 carbon atoms, bonded to the polymer skeleton via at least one linking group, and of at least one inert filler, in a cosmetic composition or for the manufacture of a physiologically acceptable composition which is solid, in particular without wax, which achieves at least one of the following characteristics: does not exude, migration-resistant deposit, non-greasy deposit, and comfortable deposit on the keratin materials.

Another subject of the invention is the use of a combination of at least one inert filler, of at least one volatile solvent and of at least one structuring polymer having a weight-average molecular mass less than 100,000, such as less than 50,000, comprising a) a polymer skeleton comprising at least one hydrocarbon-based repeating unit comprising at least one hetero atom, and b) optionally at least one terminal fatty chain and/or at least one pendant chain, optionally functionalized, comprising at least one chain chosen from alkyl and alkenyl chains, such as alkyl and alkenyl chains having at least 4 carbon atoms, and further such as alkyl and alkenyl chains having from 8 to 120 carbon atoms, bonded to the polymer skeleton via at least one linking group, in a cosmetic composition or for the manufacture of a physiologically acceptable composition, as an agent for giving to a deposit of the said composition at least one of the following characteristics: staying power or long wearing, transfer-resistance properties, and properties of not leaving marks on a support placed in contact with the said deposit.

A subject of the invention is also the use of at least one inert filler in a physiologically acceptable composition, comprising at least one structuring polymer comprising a) a polymer skeleton comprising at least one hydrocarbon-based repeating unit comprising at least one hetero atom, and b) optionally at least one terminal fatty chain and/or at least one pendant chain, optionally functionalized, comprising at least one chain chosen from alkyl and alkenyl chains, such as alkyl and alkenyl chains having at least 4 carbon atoms, and further such as alkyl and alkenyl chains having from 8 to 120 carbon atoms, bonded to the polymer skeleton via at least one linking group, as an agent for increasing at least one of the following properties of the composition: hardness, shear strength, heat resistance.

A subject of the invention is also a cosmetic process for increasing the hardness of a physiologically acceptable composition cast in particular as a stick or as a dish and/or for increasing its shear strength and/or its heat resistance, the said composition containing at least one structuring polymer comprising a) a polymer skeleton comprising at least one hydrocarbon-based repeating unit comprising at least one hetero atom, and b) optionally at least one terminal fatty chain, optionally functionalized, comprising at least one chain chosen from alkyl and alkenyl chains, such as alkyl and alkenyl chains having at least 4 carbon atoms, and further such as alkyl and alkenyl chains having from 8 to 120 carbon atoms, bonded to the polymer skeleton via at least one linking group, and c) optionally at least one pendant fatty chain, optionally functionalized, comprising at least one chain chosen from alkyl and alkenyl chains, such as alkyl and alkenyl chains having at least 4 carbon atoms, and further such as alkyl and, alkenyl chains having from 8 to 120 carbon atoms, bonded to the polymer skeleton via at least one linking group, and of at least one inert filler, which comprises introducing a sufficient amount of at least one inert filler into the composition.

Embodiments of the invention include the following: A mascara, an eyeliner, a foundation, a lipstick, a make-up-removing product, a makeup product for the body, an eyeshadow, a face powder, a concealer product, a shampoo, a conditioner, an antisun product or a care product for the lips or hair comprising a composition comprising at least one liquid fatty phase in said mascara, eyeliner, foundation, lipstick, blusher, make-up-removing product, make-up product for the body, eyeshadow, face powder, concealer product, shampoo, conditioner, antisun product or care product for the lips, hair or skin which comprises:

(i) at least one structuring polymer comprising:
  a polymer skeleton which comprises at least one hydrocarbon-based repeating unit comprising at least one hetero atom; and
(ii) at least one inert filler.

A mascara, an eyeliner, a foundation, a lipstick, a make-up-removing product, a make-up product for the body, a nail composition, an eyeshadow, a face powder, a concealer product, a shampoo, a conditioner, an antisun product or a care product for the lips, hair or nails comprising a composition comprising at least one liquid fatty phase in said mascara, eyeliner, foundation, lipstick, blusher, make-up-removing product, make-up product for the body, nail composition, eyeshadow, face powder, concealer product, shampoo, conditioner, antisun product or care product for the lips, hair or nails which comprises:

(i) at least one structuring polymer comprising:
  a polymer skeleton which comprises at least one hydrocarbon-based repeating unit comprising at least one hetero atom; and
(ii) at least one inert filler, with the proviso that said at least one inert filler is not acrylates copolymer or stearalkonium hectorite.

A deodorant product or a care product for the skin, lips, or body comprising a composition comprising at least one liquid fatty phase in said product which comprises:

(i) at least one structuring polymer comprising:
  a polymer skeleton which comprises at least one hydrocarbon-based repeating unit comprising at least one hetero atom; and
(ii) at least one inert filler, with the proviso that said at least one inert filler is not acrylates copolymer, silica, talc, or a bentonite clay.

A care product for the skin, lips, or body comprising a composition comprising at least one liquid fatty phase in said product which comprises:

(i) at least one structuring polymer comprising:
   a polymer skeleton which comprises at least one hydrocarbon-based repeating unit comprising at least one hetero atom; and
(ii) at least one inert filler.

A care and/or treatment and/or make-up composition for keratinous fibers, lips or skin comprising at least one liquid fatty phase in said care and/or treatment and/or make-up composition for keratinous fibers, lips or skin which comprises:
(i) at least one structuring polymer comprising:
   a polymer skeleton which comprises at least one hydrocarbon-based repeating unit comprising at least one hetero atom; and
(ii) at least one inert filler.

A lip composition in stick form comprising at least one continuous liquid fatty phase, at least one inert filler for the fatty phase and at least one non-waxy structuring polymer having a weight-average molecular mass of less than 100 000 in said lipstick composition, said continuous liquid fatty phase, said at least one inert filler, and said at least one non-waxy structuring polymer being present in said lipstick composition.

An eyeshadow composition comprising at least one liquid fatty phase in said eyeshadow composition which comprises:
(i) at least one structuring polymer comprising:
   a polymer skeleton which comprises at least one hydrocarbon-based repeating unit comprising at least one hetero atom; and
(ii) at least one inert filler.

A lip composition comprising at least one liquid fatty phase in said lip composition which comprises:
(i) at least one structuring polymer comprising:
   a polymer skeleton which comprises at least one hydrocarbon-based repeating unit comprising at least one hetero atom; and
(ii) at least one inert filler.

A foundation composition comprising at least one liquid fatty phase in said foundation composition which comprises:
(i) at least one structuring polymer comprising:
   a polymer skeleton which comprises at least one hydrocarbon-based repeating unit comprising at least one hetero atom; and
(ii) at least one inert filler.

A method for care, make-up or treatment of keratinous fibers, lips, or skin comprising applying to said keratinous fibers, lips, or skin a composition comprising at least one liquid fatty phase which comprises:
(i) at least one structuring polymer comprising:
   a polymer skeleton which comprises at least one hydrocarbon-based repeating unit comprising at least one hetero atom; and
(ii) at least one inert filler.

A method for providing an anhydrous composition having at least one property chosen from a solid appearance, non-exudation, shear-strength, gloss, and comfortable deposit on keratin materials chosen from lips, skin, and keratinous fibers, comprising including in said composition at least one liquid fatty phase which comprises:
(i) at least one structuring polymer comprising:
   a polymer skeleton which comprises at least one hydrocarbon-based repeating unit comprising at least one hetero atom; and
(ii) at least one inert filler, with the proviso that said at least one inert filler is not acrylates copolymer, silica, talc, or a bentonite clay.

A structured composition comprising at least one liquid fatty phase structured with at least one structuring polymer comprising a polymer skeleton comprising at least one hydrocarbon-based repeating unit comprising at least one hetero atom, wherein the at least one structuring polymer further comprises at least one chain chosen from
(i) terminal fatty chains, optionally functionalized, chosen from alkyl and alkenyl chains, bonded to the polymer skeleton via at least one linking group chosen from amides, ureas, and esters, and
(ii) pendant fatty chains, optionally functionalized, chosen from alkyl and alkenyl chains, bonded to the polymer skeleton via at least one linking group chosen from amides, ureas, and esters,
wherein when said at least one linking group is chosen from esters, said at least one terminal fatty chain is chosen from branched alkyl groups, and further comprising at least one inert filler. In one embodiment, the at least one inert filler is not acrylates copolymer, silica, talc, or a bentonite clay.

A make up or care or treatment composition for the skin, the lips, or keratinous fibers comprising a structured composition comprising at least one liquid fatty phase structured with at least one structuring polymer comprising a polymer skeleton comprising at least one hydrocarbon-based repeating unit comprising at least one hetero atom, at least one inert filler, and at least one coloring agent.

A method of making up or caring for skin, lips, or keratinous fibers comprising applying to said skin, lips, or keratinous fibers a structured composition comprising at least one liquid fatty phase structured with at least one structuring polymer comprising a polymer skeleton comprising at least one hydrocarbon-based repeating unit comprising at least one hetero atom and at least one inert filler.

A anhydrous composition comprising at least one liquid fatty phase which comprises:
(i) at least one structuring polymer comprising:
   a polymer skeleton which comprises at least three hydrocarbon-based repeating units comprising at least one hetero atom; and
(ii) at least one inert filler, including where said at least three hydrocarbon-based repeating units are identical.

A composition comprising at least one liquid fatty phase which comprises:
(i) at least one structuring polymer chosen from urea urethanes having the following formula:

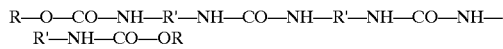

wherein R represents $C_nH_{2n+1}$-, wherein n represents an integer having a value greater than 22 or $C_mH_{2m+1}(OC_pH_{2p})_r$-, wherein m represents an integer having a value of greater than 18, p represents an integer having a value of from 2 to 4, and r represents an integer having a value of from 1 to 10.

R' represents:

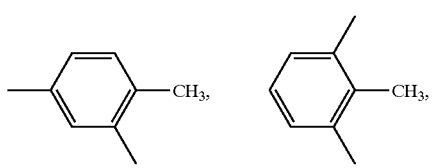

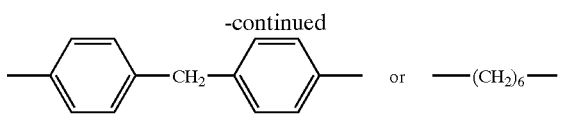

and R" represents:

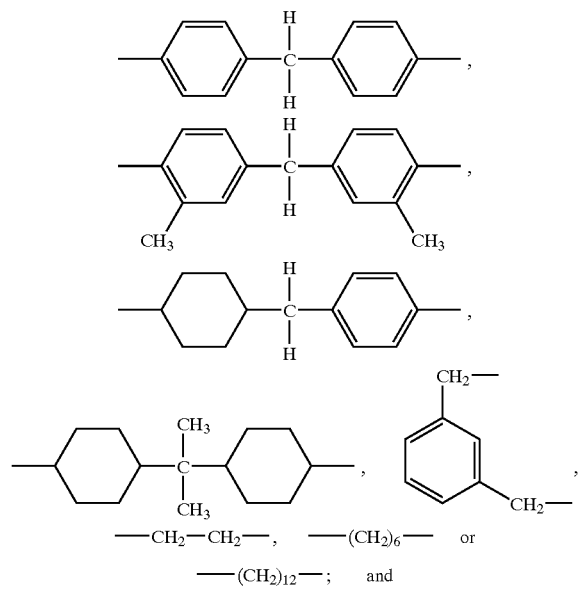

(ii) at least one inert filler.

A composition comprising at least one liquid fatty phase which comprises:

(i) at least one structuring polymer comprising:
a polymer skeleton which comprises at least one hydrocarbon-based repeating unit comprising at least one hetero atom with the proviso that said at least one hetero atom is not nitrogen; and (ii) a at least one inert filler.

A composition comprising at least one liquid fatty phase which comprises:

(i) at least one structuring polymer comprising: a polymer skeleton which comprises a) at least one hydrocarbon-based repeating unit comprising at least one hetero atom and b) at least one of:
at least one terminal fatty chain, optionally functionalized, chosen from alkyl chains and alkenyl chains, wherein said at least one terminal fatty chain is bonded to said polymer skeleton via at least one linking group; and
at least one pendant fatty chain, optionally functionalized, chosen from alkyl chains and alkenyl chains, wherein said at least one pendant fatty chain is bonded to said polymer skeleton via at least one linking group; and (ii) at least one inert filler.

A make-up composition in stick form comprising at least one continuous liquid fatty phase, at least one inert filler, and at least one non-waxy structuring polymer having a weight-average molecular mass of less than 100,000.

A method for care, make-up or treatment of keratin materials comprising applying to said keratin materials a composition comprising at least one liquid fatty phase which comprises:

(i) at least one structuring polymer comprising:
a polymer skeleton which comprises at least one hydrocarbon-based repeating unit comprising at least one hetero atom; and (ii) at least one inert filler. In one embodiment, said at least one inert filler is not acrylates polymer, silica, talc, or a bentonite clay.

A method for care, make-up or treatment of keratin fibers comprising applying to said keratin fibers a composition comprising at least one liquid fatty phase which comprises:

(i) at least one structuring polymer comprising:
a polymer skeleton which comprises at least one hydrocarbon-based repeating unit comprising at least one hetero atom; and (ii) at least one inert filler.

A method for increasing at least one of the hardness of a composition, its shear strength and its heat resistance, comprising including in said composition at least one liquid fatty phase which comprises:

(i) at least one structuring polymer comprising:
a polymer skeleton which comprises at least one hydrocarbon-based repeating unit comprising at least one hetero atom; and (ii) at least one inert filler, with the proviso that said at least one inert filler is not acrylates polymer, silica, talc, or a bentonite clay.

A method for making a physiologically acceptable cosmetic composition comprising including in a cosmetic composition at least one liquid fatty phase which comprises:

(i) at least one structuring polymer comprising:
a polymer skeleton which comprises at least one hydrocarbon-based repeating unit comprising at least one hetero atom, wherein said at least one structuring polymer further optionally comprises at least one of:
at least one terminal fatty chain comprising 8 to 120 carbon atoms, wherein said at least one terminal fatty chain is bonded to said polymer skeleton via at least one linking group; and
at least one pendant fatty chain comprising 8 to 120 carbon atoms, wherein said at least one pendant fatty chain is bonded to any carbon or hetero atom of said polymer skeleton via at least one linking group; and (ii) at least one inert filler. In one embodiment, said at least one inert filler is not acrylates polymer, silica, talc, or a bentonite clay.

A structured composition comprising at least one liquid fatty phase structured with at least one structuring polymer comprising a polymer skeleton comprising at least one hydrocarbon-based repeating unit comprising at least one hetero atom, wherein the at least one structuring polymer further comprises at least one of: terminal and pendant fatty chains, optionally functionalized, said terminal and pendant fatty chains comprising at least one chain chosen from alkyl and alkenyl chains, bonded to the polymer skeleton via at least one linking group chosen from amides, ureas, and esters, wherein when said at least one linking group is chosen from esters, said terminal fatty chains are chosen from branched alkyl groups, wherein said at least one liquid fatty phase also comprises at least one inert filler, with the proviso that said at least one inert filler is not acrylates copolymer, silica, talc, or a bentonite clay.

A structured anhydrous composition comprising at least one liquid fatty phase structured with at least one structuring polymer comprising a polymer skeleton comprising at least one hydrocarbon-based repeating unit comprising at least one hetero atom, wherein the at least one structuring polymer further comprises at least one of: terminal and pendant fatty chains, optionally functionalized, said terminal and pendant fatty chains comprising at least one chain chosen from alkyl and alkenyl chains, bonded to the polymer skeleton via at least one linking group chosen from amides, ureas, and esters, wherein when said at least one linking group is chosen from esters, said terminal fatty chains are chosen from branched alkyl groups, wherein said at least one liquid fatty phase also comprises at least one inert filler.

A skin or lip care composition comprising a structured composition comprising at least one liquid fatty phase structured in said composition with at least one structuring polymer comprising a polymer skeleton comprising at least one hydrocarbon-based repeating unit comprising at least one hetero atom, at least one inert filler, and at least one coloring agent.

A keratinous fiber treatment, care or make-up composition comprising a structured composition containing at least one liquid fatty phase structured in said composition with at least one structuring polymer comprising a polymer skeleton comprising at least one hydrocarbon-based repeating unit comprising at least one hetero atom, at least one inert filler, and at least one coloring agent.

A method of making up or caring for skin, lips or keratinous fibers comprising applying to said skin or keratinous fibers a structured composition containing at least one liquid fatty phase structured with at least one structuring polymer comprising a polymer skeleton comprising at least one hydrocarbon-based repeating unit comprising at least one hetero atom and at least one inert filler.

A composition comprising at least one liquid fatty phase in said composition which comprises:
  (i) at least one structuring polymer comprising:
    a polymer skeleton which comprises at least three hydrocarbon-based repeating units comprising at least one hetero atom; and
  (ii) at least one inert filler, with the proviso that said at least one inert filler is not silica or talc A composition comprising at least one liquid fatty phase in said composition which comprises:
  (i) at least one structuring polymer chosen from urea urethanes having the following formula:

R—O—CO—NH—R'—NH—CO—NH—R"—NH—CO—NH—R'—NH—CO—OR wherein R represents $C_nH_{2n+1}$—, wherein n represents an integer having a value greater than 22 or $C_mH_{2m+1}(OC_pH_{2p})_r$—, wherein m represents an integer having a value of greater than 18, p represents an integer having a value of from 2 to 4, and r represents an integer having a value of from 1 to 10.

R' represents:

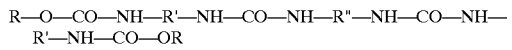

and R" represents:

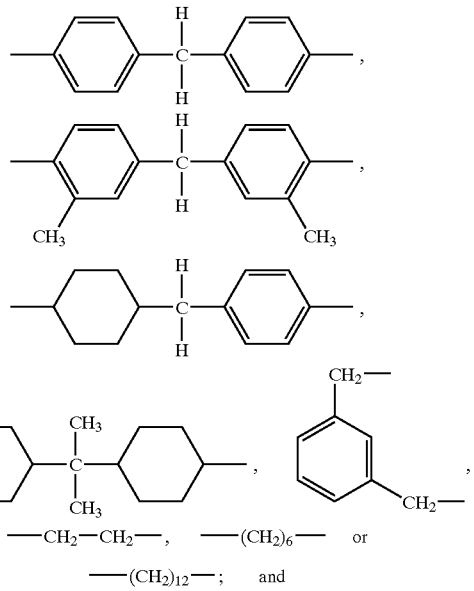

(ii) at least one inert filler.

A composition comprising at least one liquid fatty phase which comprises:
  (i) at least one structuring polymer comprising:
    a polymer skeleton which comprises at least one hydrocarbon-based repeating unit comprising at least one hetero atom; and
  (ii) at least one inert filler, with the proviso that said at least one inert filler is not acrylates copolymer, silica, talc, or a bentonite clay.

An anhydrous composition comprising at least one liquid fatty phase which comprises:
  (i) at least one structuring polymer comprising:
    a polymer skeleton which comprises at least one hydrocarbon-based repeating unit comprising at least one hetero atom; and
  (ii) at least one inert filler, with the proviso that said at least one inert filler is not acrylates copolymer or stearalkonium hectorite.

A composition comprising at least one liquid fatty phase which comprises:
  (i) at least one structuring polymer, wherein said at least one structuring polymer is at least one polyamide polymer comprising:
    a polymer skeleton which comprises at least one amide repeating unit; and
  (ii) at least one inert filler. In one embodiment, said at least one inert filler is not acrylates copolymer, silica, talc, or a bentonite clay.

The invention is illustrated in greater detail in the examples which follow. The amounts are given as percentages by mass.

EXAMPLE 1

Lipstick

| Phase A | |
|---|---|
| Uniclear 100 | 18% |
| Diisononyl isononanoate | 5% |
| Diisostearyl malate | 17% |
| Hydrogenated polybutene (Parleam) | 4% |
| Phase B | |
| Hydrophobic silica (Aerosil R972) | 3% |
| Hydrogenated polybutene | 25% |
| Isononyl isononanoate | 12% |
| Phase C | |
| Pigments | 7% |
| Hydrogenated polybutene | 9% |

Procedure

The Uniclear 100 and the oils of phase A were introduced into a heating vessel. The mixture was placed under magnetic stirring and then heated in a first stage to 100° C. (to liquefy the Uniclear). A mixture comprising the silica gel (phase B) prepared beforehand and of the ground pigmentary material (phase C), which was heated beforehand to 100° C. and homogenized with stirring, was introduced into a heated mold (T°=45° C.). The product obtained was placed, after setting had started, in a freezer (T°=−21° C.) for 15 minutes.

a) Silica gel (phase B)

The gel was prepared, with stirring in a Rayneri stirrer at 60° C., using a hotplate, by introducing the silica portion-wise into the oily mixture formed from

| Hydrogenated polybutene (Parleam) | 25 g |
|---|---|
| Isononyl isononanoate | 12 g |
| TOTAL | 40 g | b) Ground pigmentary material (phase C)

The pigments were mixed with the oil heated to 60° C.; the mixture was milled 3 times in a three-roll mill.

The sticks of lipstick had a diameter of 8.1 mm and a hardness of 77±10 gf, measured using a "cheese wire". These lipsticks were considered by testers as having good staying power and being non-greasy and glossy. This lipstick was stable and did not exude at room temperature or at 47° C., for 2 months.

The lipstick obtained deposited a glossy film with good staying power. This lipstick was considered by testers as having good staying power and being glossy.

EXAMPLES 2 TO 4

Cast Foundations

Several foundations differing from each other in the nature of the filler, and having the composition below, were prepared:

| Phase A | | |
|---|---|---|
| Uniclear 100 | | 11% |
| Isononyl isononanoate | | 10% |
| Phase B | | |
| Coated yellow iron oxide* | | 2.2% |
| Coated red iron oxide* | | 0.5% |
| Coated black iron oxide* | | 0.3% |
| Titanium oxide* | | 7% |
| Phase C | | |
| Filler | | 10% |
| Phase D | | |
| Isododecane | qs | 100% |

*The coating is aluminium stearoylglutamate

Procedure

The Uniclear 100 was incorporated into the isononyl isononanoate, with the aid of a Rayneri mixer for 10 min., in a heating vessel heated to 110° C. The stirring was continued until the Uniclear has fully dissolved (phase A).

In parallel, a pigmentary phase was prepared by incorporating 30 g of pigments (iron oxide+titanium oxide) into 8.8 g of isododecane, followed by milling using a three-roll mill. This pigmentary phase (phase B) was then introduced into phase A and the mixture was stirred until completely homogeneous, for 30 min., at 110° C. Next, the temperature was lowered to 95° C. and the volatile phase D was then added to the above mixture. After stirring the resulting mixture for 15 min., the filler (phase C) was incorporated and stirring of this mixture was then continued for 20 min. Next, the final mixture obtained was cast in foundation molds preheated to 45° C. and the mixture was then left to cool to room temperature (25° C.).

The fillers used were, respectively, silica beads (Tospearl 145 A) (Example 2), Nylon particles (Example 3) and PMMA particles of 10 to 12 μm, from Wackherr under the reference Covabead LH85® (Example 4). With the composition of Example 2, a slight phase separation was observed at room temperature after 1 month. With composition 3, good stability was obtained both at 4° C. and room temperature (25° C.) and at 45° C., after 1 month and even after 2 months, i.e., no phase separation or exudation, although the feel of this composition was not particularly pleasant. With composition 4, good stability was obtained at 4° C., 25° C. and 45° C., after 1 month and 2 months. This composition felt pleasant, non-greasy, light and fondant on the fingers and was easy to spread.

The composition of Example 4 was also compared with a commercially available transfer-resistant foundation, Teint Idole in stick form, containing conventional waxes, and no structuring polymer in the sense of the invention. These compositions were applied per half-face to 5 testers and per half-neck to 10 individuals, after applying a day cream to the face and the neck (Primordiale from Lancôme), followed by drying for 10 min. and wearing a collar made of fabric for 30 min. The extent of the deposit was assessed visually by an aesthetician. The transfer-resistance properties were graded from 0 to 7 with 0 corresponding to no deposit of foundation on the collar, and 7 corresponding to a sizeable deposit. Composition 4 according to the invention received an average score of 2.6, compared with 3 for the commercially available product, considered by the consumers as a very good transfer-resistant product in stick form. In particular, 5 testers considered that composition 4 had transfer-resistance properties that were superior to those of the commercially available product, and 3 other testers considered that composition 4 and the commercially available product had identical transfer-resistance properties.

Finally, these 2 compositions were considered as applying well, feeling soft, being comfortable and giving a natural and light make-up effect. The skin was made uniform and smooth. The make-up effect was homogeneous.

EXAMPLE 5

Cast Foundation

| | | |
|---|---|---|
| Isostearyl neopentanoate | qs | 100% |
| Isononyl isononanoate | | 15% |
| Yellow iron oxide | | 2.1% |
| Yellow-brown iron oxide | | 1% |
| Black iron oxide | | 0.3% |
| Titanium oxide (untreated anatase) | | 10.6% |
| Methyl p-hydroxybenzoate | | 0.2% |
| Talc (particle size 2 μm) | | 8.3% |
| Kaolinite (hydrated aluminium silicate) | | 3% |
| Nano-titanium oxide (particle size 2 nm) coated with PDMS | | 5% |
| Polyethylene wax MW**: 500 | | 3.7% |
| Uniclear 100 | | 7.4% |
| Hollow polymethyl methacrylate microspheres (particle size: 10 to 12 m) | | 4% |
| Polytetrafluoroethylene wax (particle size 8 μm), MW**: 75000) | | 4% |
| Octyldodecanol | | 4.4% |

**MW: number-average molecular mass.

This foundation was tested. It had the same cosmetic properties as those of the above examples.

What is claimed is:

1. A method of making up eyelashes comprising applying to said eyelashes a mascara composition comprising:
   (i) at least one inert filler chosen from at least one of kaolin and PTFE;
   (ii) at least one polymer chosen from ethylenediamine/stearyl dimer tallate copolymer;
   (iii) water;
   (iv) at least one coloring agent; and
   (iii) at least one preservative.

2. The method of making up eyelashes according to claim 1, wherein the mascara composition further comprises silica.

3. The method of making up eyelashes according to claim 1, further comprising at least one volatile solvent.

4. The method of making up eyelashes according to claim 3, wherein said at least one volatile solvent is isododecane.

5. The method of making up eyelashes according to claim 1, further comprising at least one neutralizing agent.

6. The method of making up eyelashes according to claim 1, further comprising a liquid fatty phase structured by said at least one polymer.

7. A method of making up eyelashes comprising applying to said eyelashes a mascara composition comprising:
   (i) at least one inert filler chosen from at least one of kaolin and PTFE;
   (ii) at least one polymer chosen from ethylenediamine/stearyl dimer dilinoleate copolymer;
   (iii) water;
   (iv) at least one coloring agent; and
   (v) at least one preservative.

* * * * *

UNITED STATES PATENT AND TRADEMARK OFFICE
CERTIFICATE OF CORRECTION

PATENT NO. : 6,979,469 B2
DATED : December 27, 2005
INVENTOR(S) : V. Ferrari et al.

It is certified that error appears in the above-identified patent and that said Letters Patent is hereby corrected as shown below:

<u>Title page,</u>
Item [65], Prior Publication Data,
insert -- US 2003/0161848 A1 Aug. 28, 2003 --;
"US 2004/0202683 A2 Jul. 8, 2004" should read -- US 2004/0202683 A2 Oct. 14, 2004 --.
Item [57], ABSTRACT,
Line 13, "group, $R^3$" should read -- group; $R^3$ --.

Signed and Sealed this

Eleventh Day of April, 2006

JON W. DUDAS
*Director of the United States Patent and Trademark Office*